United States Patent
Hauptmann et al.

(10) Patent No.: US 7,081,478 B2
(45) Date of Patent: Jul. 25, 2006

(54) MIXED ZEAXANTHIN ESTER CONCENTRATE AND USES THEREOF

(75) Inventors: Randal Hauptmann, Oswego, IL (US); Manuel Pavon, St. Charles, IL (US); Audrey Charles, Naperville, IL (US)

(73) Assignee: Chrysantis, Inc., West Chicago, IL (US)

( * ) Notice: Subject to any disclaimer, the term of this patent is extended or adjusted under 35 U.S.C. 154(b) by 37 days.

(21) Appl. No.: 10/453,403

(22) Filed: Jun. 3, 2003

(65) Prior Publication Data

US 2004/0022881 A1 Feb. 5, 2004

Related U.S. Application Data

(63) Continuation-in-part of application No. 10/325,265, filed on Dec. 19, 2002, which is a continuation-in-part of application No. 10/180,775, filed on Jun. 26, 2002, now Pat. No. 6,784,351.

(60) Provisional application No. 60/302,460, filed on Jun. 29, 2001.

(51) Int. Cl.
*A61K 31/22* (2006.01)
*A61K 31/07* (2006.01)

(52) U.S. Cl. ..................... 514/546; 514/725
(58) Field of Classification Search ............... 514/546, 514/725
See application file for complete search history.

(56) References Cited

U.S. PATENT DOCUMENTS

| | | |
|---|---|---|
| 2,918,370 A | 12/1959 | Helgren |
| 4,670,247 A | 6/1987 | Scialpi |
| 5,043,170 A | 8/1991 | Borenstein et al. |
| 5,258,189 A | 11/1993 | Efstathiou |
| 5,270,063 A | 12/1993 | Wullschleger et al. |
| 5,290,605 A | 3/1994 | Shapira |
| 5,308,759 A | 5/1994 | Gierhart |
| 5,382,714 A | 1/1995 | Khachik |
| 5,427,783 A | 6/1995 | Gierhart |
| 5,523,494 A | 6/1996 | Torres-Cardona et al. |
| 5,536,504 A * | 7/1996 | Eugster et al. ............. 424/450 |
| 5,605,699 A | 2/1997 | Bernhard et al. |
| 5,618,988 A | 4/1997 | Hauptmann et al. |
| 5,648,564 A | 7/1997 | Ausich et al. |
| 5,684,238 A | 11/1997 | Ausich et al. |
| 5,695,794 A | 12/1997 | Stark et al. |
| 5,747,544 A | 5/1998 | Garnett et al. |
| 5,811,273 A | 9/1998 | Misawa et al. |
| 5,827,652 A | 10/1998 | Garnett et al. |
| 5,849,345 A | 12/1998 | Giger et al. |
| 5,854,015 A | 12/1998 | Garnett et al. |
| 5,858,700 A | 1/1999 | Ausich et al. |
| 5,910,433 A | 6/1999 | Kajiwara et al. |
| 5,935,624 A | 8/1999 | DeLuca et al. |
| 5,955,102 A | 9/1999 | Gorenbein et al. |
| 5,965,795 A | 10/1999 | Hirschberg et al. |
| 5,972,690 A | 10/1999 | Misawa et al. |
| 6,056,962 A | 5/2000 | Kesharlial et al. |
| 6,150,130 A | 11/2000 | Misawa et al. |
| 6,191,293 B1 | 2/2001 | Levy |
| 6,218,436 B1 | 4/2001 | Howard et al. |
| 6,224,876 B1 | 5/2001 | Kesharlal et al. |
| 6,254,898 B1 | 7/2001 | Bragaglia |
| 6,262,284 B1 | 7/2001 | Khachik |
| 6,329,432 B1 | 12/2001 | Howard et al. |
| 6,383,474 B1 | 5/2002 | Soudant et al. |
| RE38,009 E | 2/2003 | Garnett et al. |
| 2004/0010826 A1 | 1/2004 | Hauptmann et al. |

FOREIGN PATENT DOCUMENTS

| | | |
|---|---|---|
| DE | 4020874 | 1/1991 |
| WO | WO 91/03571 | 3/1991 |
| WO | WO 92/16635 | 10/1992 |
| WO | WO 96/40092 | 12/1996 |
| WO | WO 99/61652 | 12/1999 |
| WO | WO 00/32788 | 6/2000 |

OTHER PUBLICATIONS (Abstract Only) Cirilli et al., Technica Molitoria (1975), 26(7), 79-82.*
Zaharia, et al., "Actiunea Radiathlor Gamma Asupra Germinatiei Si Biosintezei Pigmentilor Asimilatori Oa Unele Plante Floricole", *Seria Agricultura*, 44(1):107-114 (1991).
Tyczkowski et al., "Research Note: Preparation of Purified Lutein and Its Diesters from Extracts of Marigold (*Tagetes erecta*)", *Poultry Sci.*, 70(3):651-654 (1991).
Quackenbush et al., "Vitamins and Other Nutrients: Composition and Analysis of the Carotenoids in Marigold Petals", *J. Assoc. Off. Anal. Chem.*, 55(3):617-621 (1972).
Geetha et al., "Induced Chlorophyll and Viable Mutations in Targetes Patula L.", *Acta Botanica Indica*, 20(2):312-314 (1992).

(Continued)

*Primary Examiner*—Raymond J. Henley, III
(74) *Attorney, Agent, or Firm*—Welsh & Katz, Ltd.

(57) ABSTRACT

Mixed zeaxanthin $C_8$–$C_{20}$ carboxylic acid esters in which the mixed zeaxanthin esters constitute about 50 mg/g or more of the concentrate and wherein the zeaxanthin is about 20 percent or more of the total carotenoids present when assayed after saponification are disclosed, as are the products that can be made from such a concentrate, as well as the several uses for mixed zeaxanthin esters.

21 Claims, 1 Drawing Sheet

OTHER PUBLICATIONS

Khachik et al., "Separation and Identification of Carotenoids and Their Oxidation Products in the Extracts of Human Plasma", *Anal. Chem.*, 64:2111-2122, (no date available).

Jyonouchi et al., "Studies of Immunomodulating Actions of Carotenoids, II. Astaxanthin Enhances *In Vitro* Antibody Production to T-Dependent Antigens Without Facilitating Polyclonal B-Cell Activation", *Nutrition and Cancer*, 19(3):269-280 (1993).

Fray et al., "Identification and Genetics Analysis of Normal and Mutant Phytoene Synthase Genes of Tomato by Sequencing, Complementation and Co-Suppression", *Plant Mol. Biol.*, 22:589-602 (1993).

Bone et al., "Stereochemistry of the Human Macular Carotenoids", *Invest. Ophthalmol. Vis. Sci.*, 34(6):2033-2040 (1993).

Finnegan et al., "Transgene Inactivation: Plants Fight Back!", *Bio/Technology*, 12:883-888 (1994).

Tanaka et al., "Chemoprevention of Mouse Urinary bladder Carcinogenesis by the Naturally Occurring Carotenoid Astaxanthin", *Carcinogenesis*, 15(1):15-19 (1994).

Seddon et al., "Dietary Carotenoids, Vitamins A, C, and E, and Advanced Age-Related Macular Degeneration", *JAMA*, 272(18):1413-1420 (1994).

Morris et al., "Serum Carotenoids and Coronary Heart Disease: The Lipid Research Clinics Coronary Primary Prevention Trial and Follow-Up Study", *JAMA*, 272(18):1439-1441 (1994).

Khachik et al., "Lutein, Lycopene, and Their Oxidative Metabolites in Chemoprevention of Cancer", *J. Cellular Biochem.*, 22:236-246 (1995).

Balnave et al., "Relative Efficiencies of Yellow Carotenoids for Egg Yolk Pigmentation", *AJAS*, 9(5):515-517 (1996).

Pogson et al., "Arabidopsis Carotenoid Mutants Demostrate that Lutein is Not Essential for Photosynthesis in Higher Plants", *Plant Cell*, 8:1627-1639 (1996).

Bone et al., "Distribution of Lutein and Zeaxanthin Stereoisomers in the Human Retina", *Exp. Eye. Res.*, 64(2):211-218 (1997).

Khachik et al., "Identification, Quantification, and Relative Concentrations of Carotenoids and Their Metabolites in Human Milk and Serum", *Anal. Chem.*, 69:1873-1881.

Piccaglia et al., "Lutein and Lutein Ester Content in Different Types of *Tagetes patula* and T. Erecta", *Ind. Crops and Prod.*, 8:45-51 (1998).

Moehs, et al., "Analysis of Carotenoid Biosynthesis Gene Expression During Marigold Petal Development", *Plant Mol. Biol.*, 45:281-293 (2001).

Bernstein et al., "Identification and Quantitation of Carotenoids and Their Metabolites in the Tissues of the Human Eye", *Exp. Eye Res.*, 72:215-223 (2001).

AOAC 1984, *Official Methods of Analysis* (14th Ed.), the Association of Official Analytical Chemists, Arlington, VA, USA, (no date available).

Bone et al., "Analysis of the Macular Pigment by HPLC: Retinal Distribution and Age Study", *Invest Ophthalmol. Vis. Sci.*, 29(6):843-849 (1998).

Giovannucci et al., "Intake of Carotenoids and Retinol in Relation to Risk of Prostate Cancer", *J. Nat. Cancer Inst.*, 87(23):1767-1776 (1995).

Datta, et al., "Short Communication: Gamma Ray-Induced Genetic Manipulations in Flower Colour and Shape in *Dendrathema grandiflorum* and Their Management Through Tissue Culture", *Plant Breeding*, 120:91-92 (2001).

Masakazu et al., "The Effects of Irradiating Gladiolus (Gladiolus X Grandiflora Hort.) Cormels with Gamma Rays on Callus Formation, Somatic Embryogenesis and Flower Color Variations in the Regenerated Plants", *J. Japanese Soc. of Hort. Sci.*, 70(1):126-128 (2001).

Venkatachalam et al., "Effect of Gamma Rays on Some Qualitative and Quantitative Characters in Zinnia Elegans Jacq.", *Ind. J. Gen. & Plant Breeding*, 57(3):255-261 (1997).

Li et al., "A Fast Neutron Deletion Mutagenesis-Based Reverse Genetics System for Plants", *Plant Journal*, 27(3):235-242 (2001).

Love et al., "The Induction of Bud Sports in *Coleus blumei* by Fast Neutrons", *Amer. Soc. Hort. Sci.*, 88:627-630 (1966).

Abe et al., *In Vitro Cell. & Dev. Bio.*, 38:93A (2002), Abstract P-1283.

Meyer et al., "Differences in DNA-Methylation are Associated with a Paramutation Phenomenon in Transgenic Petunia", *Plant Journal*, 4(1):89-100 (1993).

Napoli et al., "Introduction of a Chimeric Chalcone Synthase Gene into Petunia Results in Reversible Co-Suppression of Homologous Genes *in trans*", *Plant Cell*, 2:279-289 (1990).

Jorgensen et al., "Chalcone Synthase Cosuppression Phenotypes in Petunia Flowers: Comparison of Sense vs. Antisense Constructs and Single-Copy vs. Complex T-DNA Sequences", *Plant Mol. Biol.*, 31:957-973 (1996).

Hamilton et al., "A Species of Small Antisense RNA in Posttranscriptional Gene Silencing in Plants", *Science*, 286:950-952 (1999).

Metzlaff et al., "RNA-Mediated RNA Degradation and Chalcone Synthase A Silencing in Petunia", *Cell*, 88:845-854 (1997).

Chuang et al., "Specific and Heritable Genetic Interference by Double-Stranded RNA in *Arabidopsis thaliana*", *PNAS*, 97(9):4985-4990.

Wesley et al., "Construct Design for Efficient, Effective and High-Throughput Gene Silencing in Plants", *Plant Journal*, 27(6);581-590 (2001).

Yang et al., "Ribozyme-Mediated High Resistance Against Potato Spindle Tuber Viroid in Transgenic Potatoes", *Proc, Natl. Acad. Sci.*, 94:4861-4865 (1997).

Miki et al., "Procedures for Introducing Foreign DNA into Plants", in *Methods in Plant Molecular Biology and Biotechnology*, Glick et al., Eds., CRC Press, Boca Raton, Florida, pp. 67-88 (1993).

Klein et al., "Transformation of Microbes, Plants and Animals by Particle Bombardment", *Bio/Technology*, 10:286-291 (1992).

Horsch et al., "A Simple and General Method for Transferring Genes into Plants", *Science*, 227:1229-1231 (1985).

Gruber et al., "Vectors for Plant Transformation", in *Methods in Plant Molecular Biology and Biotechnology*, Glick et al., Eds., CRC Press, Boca Raton, Florida, pp. 89-119 (1993).

Moloney et al., "High Efficiency Transformation of *Brassica napus* Using *Agrobacterium* Vectors", *Plant Cell Reports*, 8:238-242 (1989).

Lotan, et al., "Cloning and Expression in *Escherichia coli* of the Gene Encoding β-C-4-Oxygenase, that Converts β-Carotene to the *Ketocarotenoid canthaxanthin* in *Haematococcus pluvialis*", *FEBS Letters*, 364:125-128 (1995).

Fraser, et al., "Enzymic Confirmation of Reactions Involved in Routes to Astaxanthin Formation, Elucidated Using a Direct Substrate in Vitro Assay", *Eur. J. Biochem.*, 252:229-236 (1998).

Misawa et al., "Elucidation of the *Erwinia uredovora* Carotenoid Biosynthetic Pathway by Functional Analysis of Gene Products Expressed in *Escherichia coli*", *J. Bacteriology*, 172(12):6704-6712 (1990).

Misawa et al., "Production of β-Carotene in Zymomonas Mobilis and Agrobacterium Tumefaciens by Introduction of the Biosynthesis Genes from *Erwinia uredovora*", *Applied and Environmental Microbiology*, 57(6):1847-1849 (1991).

*Hortus Third A Concise Dictionary of Plants Cultivated in the United States and Canada*, MacMillan Publishing Company (1976).

W.I. Marusich et al., "Zeaxanthin as a Broiler Pigmenter", *Poultry Sci.*, 55:1486-1494 (1980).

Cetl et al, "Genetic and Cytogenetic Problems of *Tagates* L. Breeding", *Folia Fac. Sci. Nat. Univ. Purkynianae Brun. Biol.*, 21(1):5-56 (1985).

Bone et al., "Preliminary Identification of the Human Macular Pigment", *Vision Res.*, 25(11):1531-1535 (1985).

Jyonouchi et al., "Studies of Immunomodulating Actions of Carotenoids. I. Effects of β-Carotene and Astaxanthin on Murine Lymphocyte Functions and Cell Surface Marker Expression in *In Vitro* Culture System", *Nutrition and Cancer*, 16)2):93-105 (1991).

Diaconu, "Utilization of Induced Variation in Breeding Pot Marigolds", *Agronomie*, 34(1):17-21 (1991).

Heslot, H. 1966. Mutation Induction by Physical and Chemical Mutagenic Agents. Mutat. Plant. Breed., Proc. Panel. pp. 139-149.

Lewin, B. 1985. Genes. John Wiley & Sons. 2nd. ed. p. 45.

Medina et al. Marigold Flower Meal as a Source of an Emulsifying Gum. [online], [retrieved on Dec. 1, 2004]. Retrieved from the Internet <http://www.hort.purdue.edu/newcrop/proceedings1993/v2-389.html>.

* cited by examiner

MIXED ZEAXANTHIN ESTER CONCENTRATE AND USES THEREOF

CROSS-REFERENCE TO RELATED APPLICATIONS

This is a continuation-in-part of application Ser. No. 10/325,265 filed on Dec. 19, 2002 entitled "*Tagetes erecta* MARIGOLDS WITH ALTERED CAROTENOID COMPOSITIONS AND RATIOS" that is a continuation-in-part of application Ser. No. 10/180,775 that was filed on Jun. 26, 2002, now U.S. Pat. No. 6,784,351 that claimed priority from provisional application Serial No. 60/302,460 that was filed on Jun. 29, 2001.

DESCRIPTION

1. Technical Field

The present invention relates to mixed zeaxanthin esters. The invention more particularly relates to mixed zeaxanthin esters in the form of a concentrate and the products that can be made from such a concentrate, as well as the several uses for mixed zeaxanthin esters.

2. Background of the Invention

Carotenoids have long been described as natural antioxidants that are known to quench free radicals before the free radicals attack healthy cells. More specifically, an antioxidant is a substance that significantly decreases the adverse effects of reactive species, such as reactive oxygen and nitrogen species, on the normal physiological function. Several highly oxidizing species are generated in biological systems, including singlet oxygen, hydroxyl radical, superoxide, hydrogen peroxide, organic hyperoxides and peroxyl radicals. These species can react with carotenoids by three distinctly different pathways: electron transfer, hydrogen abstraction, and radical addition [See Krinsky et al., *Annual Rev. Nutr.*, 23:171–201 (2003).]

Carotenoids in general and specific carotenoids such as lycopene, lutein and zeaxanthin, have demonstrated use as antioxidants in compositions that can be administered to provide beneficial protection against health-damaging effects of free radicals. Such benefits include protecting the body from skin, eye, liver, and lung damage, and certain forms of cancer. Free radicals are unstable chemicals formed in the body during metabolism and from exposure to environmental sources, such as air pollution, cigarette smoke, sunlight and dietary fats. When there are an excessive number of free radicals in the body, free radicals can attack healthy cells and can contribute to a number of degenerative diseases, such as cancer and crosslinking of collagen.

Free radicals have been linked to numerous diseases and health conditions. Conditions associated with free radicals and affecting multiple organs include: inflammatory-immune injury; alcohol damage; radiation injury; aging (premature aging disorders, age-related immunodeficiency); and cancer. Conditions relating to specific organs or tissues and associated with free radicals include: rheumatoid arthritis, atherosclerosis, senile dementia, Alzheimer's disease, Parkinson's disease (MPTP), muscular sclerosis, cataractogenisis, degenerative retinal damage, and solar radiation.

Zeaxanthin has been identified as a macular pigment of the retina and as having a functional role of protecting the retina against light-induced damage. Bernstein et al., *Exp. Eye Res.*, 72(3):215–223 (2001) extracted carotenoids from ocular tissues [retinal pigment epithelium/choroid (RPE/choroid), macula, peripheral retina, ciliary body, iris, lens, vitreous, cornea, and sclera] for analysis by high-performance liquid chromatography (HPLC). Nearly all ocular structures examined with the exception of vitreous, cornea, and sclera had quantifiable levels of dietary (3R,3'R,6'R)-lutein, zeaxanthin, their geometrical (E/Z) isomers, as well as their metabolites, (3R,3'S,6'R)-lutein (3'-epilutein) and 3-hydroxy-beta, epsilon-caroten-3'-one. Uveal structures (iris, ciliary body, and RPE/choroid) accounted for approximately 50 percent of the eye's total carotenoids and approximately 30 percent of the lutein and zeaxanthin.

The predominant carotenoids of the macular pigment are lutein, zeaxanthin, and meso-zeaxanthin. The regular distribution pattern of these carotenoids within the human macula indicates that their deposition is actively controlled in this tissue. Increased macular carotenoid levels result from supplementation of humans with lutein and zeaxanthin. [See Landrum et al., *Arch. Biochem. Biophys.*, 385(1):28–40 (2001).]

Zeaxanthin extracted from the macula has been shown to consist of similar amounts of the (3R, 3'R) and (3R, 3'S) stereoisomers and small quantities of the (3S,3'S)-zeaxanthin stereoisomer in the adult retina, particularly in the macula (the retinal region responsible for fine visual activities). It was proposed that dietary lutein and zeaxanthin are transported into an individual's retina in the same proportions found in the blood serum, although the two pigments are present in the eye in ratios different from those found in the blood. [See Bone et al., *Invest. Ophthalmol. Vis. Sci.*, 34:2033–2040 (1993) and Bone et al., *Exp. Eye Res.*, 64(2): 211–218 (1997).] Thus, zeaxanthin predominates over lutein by a ratio greater than 2:1 in the foveal region, with the macular pigment optical density dropping by a factor of 100 and the zeaxanthin to lutein ratio reversing to about 1:2. [See Bone et al., *Invest. Ophthalmol. Vis. Sci.*, 29:843–849 (1988).] It has been suggested that some lutein is converted into the non-dietary meso-zeaxanthin primarily in the macula, by a mechanism that is less developed in infants than adults. [See Bone et al., *Exp. Eye Res.*, 64(2):211–218 (1997).]

There is increasing evidence that the macular pigment carotenoids, lutein and zeaxanthin, can play an important role in the prevention of age-related macular degeneration (ARMD), cataract formation, and other light-induced oxidative eye damage. In 1985 and 1993, Bone et al. demonstrated that the human macular pigment is a combination of lutein and zeaxanthin, and speculated that these dietary carotenoids play a role in the prevention of an eye disease ARMD. [See Bone et al., *Vision Research*, 25:1531–1535 (1985) and Bone et al., *Invest. Ophthalmol. Vis. Sci.*, 34:2033–2040 (1993).] Further work in a case-controlled epidemiological study in which the high consumption of fruits and vegetables, rich specifically in lutein and zeaxanthin was correlated to a 43 percent lower risk of ARMD later confirmed that speculation. [See Seddon et al., *J. A. Med. Assoc.*, 272(18):1413–1420 (1994).] It has also been reported that an increased level of serum carotenoids other than β-carotene is associated with a lower incidence of heart disease. [See Morris et al., *J. Amer. Med. Assoc.*, 272(18): 1439–1441(1994).]

Ingestion of purified supplements of dietary (3R,3'R,6'R)-lutein and (3R,3'R)-zeaxanthin was shown to not only result in an increase in the serum levels of these compounds in humans, but also in an increase in the concentration of their oxidative metabolites in plasma. [See Khachik et al., *J. Cellular Biochem.*, 22:236–246 (1995).] These findings provided preliminary evidence that carotenoids can function as antioxidants in disease prevention. In addition, these results also established the importance of non-vitamin A-active dietary carotenoids, particularly, lutein, zeaxanthin, and lycopene.

The presence of the direct oxidation product of lutein and 3'-epilutein (metabolite of lutein and zeaxanthin) in human retina suggests that lutein and zeaxanthin act as antioxidants to protect the macula against short-wavelength visible light.

An oxidative-reductive pathway for lutein and zeaxanthin in human retina, can therefore play an important role in prevention of age-related macular degeneration and cataracts. [See Khachik et al., *Invest Ophthalmol Vis Sci* 38(9):1802–11 (1997).]

Researchers at the Schepens Eye Research Institute and Department of Ophthalmology, Harvard Medical School report that dietary zeaxanthin plays an essential role in protecting the retina from light damage. [See Thomson et al., *Invest. Ophthalmol. Vis. Sci.*, 43(11):3538–49 (2002).] Thus, it was previously theorized that the two carotenoids found in high concentrations in the macula, zeaxanthin and lutein, protect the retina because of their ability to absorb harmful blue light and their status as powerful antioxidants.

Although some clinical studies have found evidence that people with higher dietary or serum levels of zeaxanthin and lutein had reduced risk for advanced stages of age-related macular degeneration (AMD), others have found no association. Thomson et al., above, provided the first direct experimental evidence that carotenoids protect the retina using Japanese quail, because the retina resembles the human macula in having more cone photoreceptors than rods, and in highly selective accumulation of zeaxanthin and lutein from their diet. The studies examined the effect of manipulating dietary carotenoids on light damage to retinas by raising quail on diets that were normal, carotenoid-deficient, or carotenoid-deficient supplemented with high doses of zeaxanthin. These studies established that photo-protection was strongly correlated with the concentration of zeaxanthin in the retinas of the quail. In a short-term study, retinas with low concentrations of zeaxanthin suffered severe light damage, as evidenced by a very high number of apoptotic photoreceptor cells, whereas the group with high zeaxanthin concentrations had minimal damage.

In these long-term studies, groups of quail were raised for six months on carotenoid-deficient, normal or zeaxanthin-supplemented diets before exposure to brighter light. The results showed extensive damage to the retina in the carotenoid-deficient animals, as evidenced by large numbers of both dying photoreceptors and gaps or "ghosts" marking sites where photoreceptors had died. The group of quail with normal dietary levels of zeaxanthin showed significantly less retinal damage than did the zeaxanthin-deprived group, whereas the quail group receiving high levels of zeaxanthin had few ghosts in their retinas.

These studies showed protection of both rod and cone photoreceptors. The research further demonstrated that retinas were protected by both zeaxanthin and another antioxidant, vitamin E. Damage in these experiments was clearly reduced by zeaxanthin and tocopherol, but not lutein.

Hammond et al., *Invest. Ophthalmol. Vis. Sci.*, 38(9): 1795–1801 (1997) studied macular pigment measured psychophysically in 13 subjects. Serum concentrations of lutein, zeaxanthin, and beta-carotene were measured by high-performance liquid chromatography. Eleven subjects modified their usual daily diets by adding 60 g of spinach (10.8 mg lutein, 0.3 mg zeaxanthin, 5 mg beta-carotene) and ten also added 150 g of corn (0.3 mg zeaxanthin, 0.4 mg lutein); with two other subjects being given only corn. Dietary modification lasted up to 15 weeks.

Increases in macular pigment density were obtained within 4 weeks of dietary modification for most, but not all, subjects. Most subjects fed spinach or spinach plus corn responded with both serum and macular pigment density enhancements, although some only evidenced macular pigment enhancement, whereas one showed no change in either serum of macular pigment. Those receiving only corn supplements showed little, if any, enhancement of serum lutein, with one subject exhibiting a large increase in serum zeaxanthin and a smaller, but relatively large increase in macular pigment density. When macular pigment density increased with dietary modification, it remained elevated for at least several months after resuming an unmodified diet.

Inventors from B.V. Werklust & Beheer suggest the use of xanthophylls esters for the prevention and treatment of eye diseases in patent application DE 199 50 327. Ester stability studies were described for synthetically derived short chain fatty acids. No mention was made of longer chain fatty acid esters.

A study involving 77,466 female nurses reported a decreased risk of cataract extraction associated with increased lutein and zeaxanthin intake. [See Chasan-Taber et al., *Am. J. Clin. Nutr.*, 70:509–516 (1999).] In addition, a decrease in cataract extraction was reported for men in the highest quintile of lutein and zeaxanthin intake. [See Brown et al., *Am. J. Clin. Nutr.*, 70:517–524 (1999).]

Reports of anti-carcinogenic activity of zeaxanthin are recent. Zeaxanthin suppressed TPA-induced expression of early antigen of Epstein-Barr virus in Raji cells. Zeaxanthin also inhibited TPA-enhanced $^{32}$Pi-incorporation into phospholipids of cultured cells. In an in vivo study, it was found that spontaneous liver carcinogenesis in C3H/He male mice was suppressed by the treatment with zeaxanthin at the concentration of 0.005 percent mixed as an emulsion with drinking water [See Nishino et al., *Cancer and Metastasis Reviews*, 21:257–264 (2002).]

Antioxidative effects of other carotenoids are known. U.S. Pat. No. 6,383,474 to Soudant et al. teaches that phytoene and phytofluene, used in combination, are effective in preventing damage caused from oxidation and exposure to UV light. This combination is said to be useful as a topical preparation, as a pharmaceutical or as a food additive.

β-Carotene and lycopene are well-known food additives, with lycopene consumption recently being reported to provide a reduced risk of prostate cancer. [See Giovannucci et al., *J. Natl. Cancer Inst.*, 87(23):1767–1776 (1995).] Lycopene is naturally present as the red pigment in tomato skins, whereas β-carotene is the primary carotenoid pigment in carrots. Hauptmann et al. U.S. Pat. No. 5,618,988 teaches the preparation of carotenoid pigments such as β-carotene in storage organs of transformed plants such as carrots. Ausich et al. U.S. Pat. No. 5,858,700 teaches the isolation of lycopene crystals from an oleoresin as can be prepared from tomato skins. The structural formulas of lycopene and β-carotene are shown below.

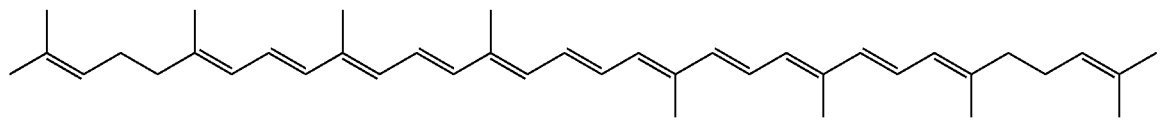

Lycopene

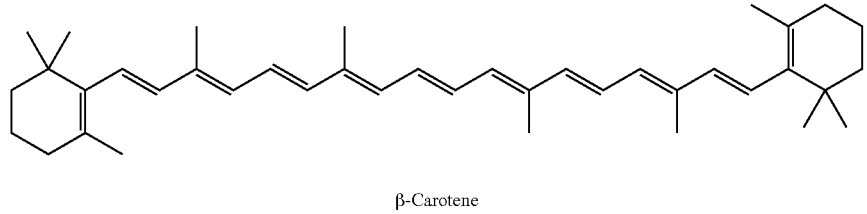

β-Carotene

Astaxanthin, a red xanthophyll whose structural formula is shown below, is widely used as a pigmenting agent for cultured fish and shellfish. The complete biomedical properties of

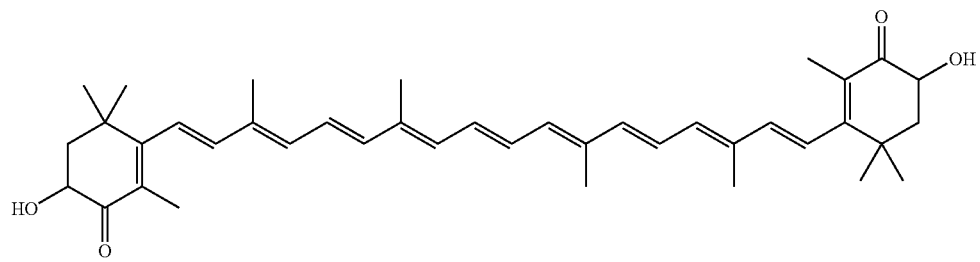

Astaxanthin astaxanthin remain to be elucidated, but initial results suggest that it could play an important role in cancer and tumor prevention, as well as eliciting a positive response from the immune system. [See Tanaka et al., *Carcinogenesis* 15(1): 15–19 (1994), Jyonouchi et al., *Nutrition and Cancer* 19(3): 269–280 (1993) and Jyonouchi et al., *Nutrition and Cancer* 16(2): 93–105 (1991).]

Carotenoids from food sources have lower bioavailability and absorption than diet supplementation with pure carotenoids. In supplements, xanthophylls can be provided in ester or unesterified forms. Lutein bioavailability has been determined for lutein diester and unesterified lutein formulations as they might be incorporated into human dietary supplements. For most individuals studied, lutein provided by a particular lutein diester formulation was more bioavailable than was lutein provided by a formulation containing free lutein. The authors concluded that the lutein diester formulation posed no impediment to lutein bioavailability at the doses tested. A comparison with data from previous studies suggested that formulation dissolution was a greater limitation to bioavailability than lutein ester hydrolysis. An oil-solubilized unesterified lutein preparation resulted in greater bioavailability compared with either the unesterified or lutein diester formulations of the reported study [See Bowen et al. *J. Nutr.* 132:3668–3673 (2002) and Bowen and Clark U.S. Pat. No. 6,313,169.]

The richest source of lutein found in nature is the marigold flower, *Tagetes erecta*, which typically contains 3 to 5 percent zeaxanthin esters. The *Tagetes* genus is a member of the family Compositae, alternatively known as Asteraceae, and comprises some thirty species of strongly scented annual or perennial herbs. *Tagetes* are native from Arizona and New Mexico to Argentina. [See *Hortus Third A Concise Dictionary of Plants Cultivated in the United States and Canada*, MacMillan Publishing Company (1976).] Cultivated species include *Tagetes erecta*, commonly referred to as African marigold, *Tagetes patula*, commonly referred to as French marigold, *Tagetes erecta* x *patula*, commonly referred to as Triploid marigolds, and *Tagetes tenuifolia* also known as *Tagetes signata* or signet marigold.

A marigold inflorescence is a solitary head comprised of a dense cluster of several hundred sessile or subsessile small flowers also known as florets. Marigolds have radiate flower heads with outer ray florets that are ligulate or strap-shaped around the central tubular shaped disk florets. Some forms of marigold flower heads have most of their disk flowers transformed into ray flowers and contain few, if any, disk flowers. Such flower heads are referred to as double-flowered.

The ray flowers or florets are often referred to as petals by lay persons who also refer to the flower heads as flowers. For ease of understanding, marigold flower heads will be referred to herein as flowers or flower heads, whereas the flower head-component flowers or florets, stamens, stigmas and carpels will be referred to as petals.

Cultivated marigolds possess showy flowers and are useful for ornamental purposes. In addition, the genus is recognized as a source for natural colorants, essential oils, and thiophenes. Dried marigold petals and marigold petal concentrates obtained from so-called xanthophyll marigolds are used as feed additives in the poultry industry to intensify the yellow color of egg yolks and broiler skin. [See Piccalia et al., *Ind. Crops and Prod.*, 8:45–51 (1998).] The carotenoids desired in poultry tissues are a function of their dietary concentration, because poultry do not have the ability to synthesize carotenoids de novo. [See Balnave et al., *Asian-Australiasian J. Animal Sci.*, 9(5):515–517 (1996).]

Xanthophyll marigolds differ in several characteristics from ornamental marigolds. First and foremost, xanthophyll marigolds are used as an extractable source for carotenoids and have plant habits that differ from ornamental marigolds. Ornamental marigolds typically grow only about 45 to about 60 cm from the ground, whereas xanthophyll marigolds grow to about 65 to about 70 cm from the ground. Xanthophyll marigolds grow in a bushier habit than do ornamental marigolds, and can be grown as row crops whereas ornamental marigolds typically cannot. Xanthophyll marigolds are typically dark orange in color, whereas ornamentals can be white, yellow, or orange in color, or can have mixed colors, including mahogany colors due to the presence of anthocyanin pigments.

The pigmenting ability of marigold petal meal resides largely in the oxygenated carotenoid fraction known as the xanthophylls, primarily lutein esters. [See Piccalia et al., *Ind. Crops and Prod.*, 8:45–51 (1998).] The xanthophyll zeaxanthin, also found in marigold petals, has been shown to be effective as a broiler pigmenter, producing a highly acceptable yellow to yellow-orange color. [See Marusich et al., *Poultry Sci.*, 55:1486–1494 (1976).] Of the xanthophylls, the pigments lutein and zeaxanthin are the most abundant in commercially available hybrids. Structural formulas for lutein and zeaxanthin are shown below.

cial varieties include 'Orangeade', one of the original xanthophyll producing varieties, and commercial improvements of 'Orangeade', including 'Deep Orangeade' having larger flowers and greater pigment yields, and 'Scarletade' an improvement for xanthophyll concentration. Thus, 'Orangeade' is reported to contain xanthophylls at about 9–12 mg/g of dry whole flower heads (including calyx), 'Deep Orangeade' is reported to have about 10–13 mg/g of those pigments, and 'Scarletade' is said to contain about 12–18 mg/g of xanthophyll pigments in dry flower heads weighed with the calyx. These varieties are available from PanAmerican Seed Co., 622 Town Road, West Chicago, Ill. 60185.

Whereas lutein is the major xanthophyll in marigold flowers, some current varieties yield extract products with zeaxanthin ratios {[zeaxanthin/(lutein+zeaxanthin)]×100%}

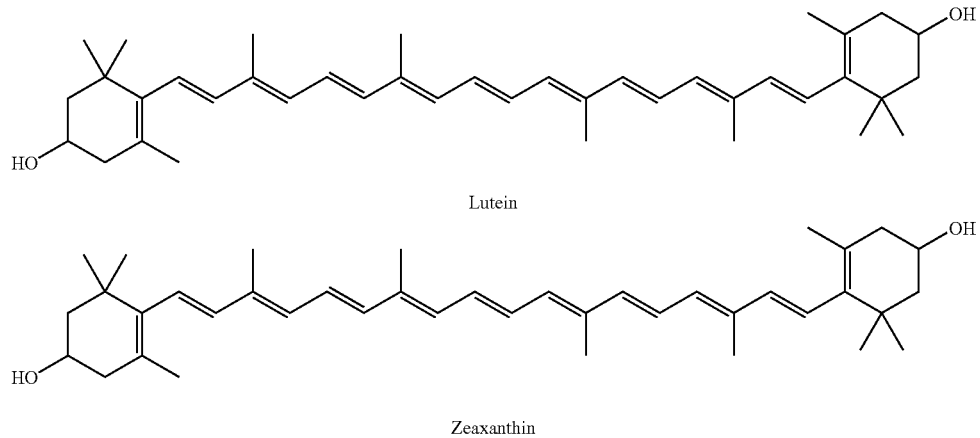

Lutein

Zeaxanthin

Each of lutein and zeaxanthin contains one hydroxyl group in each of their terminal ring structures, so that each molecule contains two hydroxyl groups. Lutein is believed to be biologically produced by two separate hydroxylations of α-carotene, whereas zeaxanthin is believed to be biologically produced by two separate hydroxylations of β-carotene.

Both α-carotene and β-carotene are understood to be formed by the action of appropriate cyclase enzymes on lycopene to first yield δ-carotene or γ-carotene that thereafter cyclize further to form α-carotene or β-carotene, respectively. Lycopene, β-carotene, α-carotene and β-carotene are each hydrocarbon carotenoids that are referred to in the art as carotenes. Thus, carotenoid pigments can be grouped into one or the other of two families: the hydrocarbon carotenes or the oxygenated xanthophylls. Phytoene, the first $C_{40}$ carotenoid in the pathway, is a colorless hydrocarbon. The hydrocarbon carotene pigments with the exception of β-carotene typically do not accumulate in marigold leaves or flower parts, whereas the xanthophylls do accumulate in both leaves and flower parts.

FIG. 1 shows a schematic representation of the biological synthesis pathway for the production of lutein and zeaxanthin and later products from phytoene via lycopene, γ-carotene, α-carotene and β-carotene. Lutein and zeaxanthin are present in marigold petals primarily as mono- and di-esters of fatty acids. FIG. 1 also notes epoxide-containing later products that can arise from zeaxanthin, of which violaxanthin is an intermediate in the abscisic acid biosynthetic pathway.

Xanthophyll marigolds are produced primarily in Mexico, Peru, Africa, India, China and Thailand. Modern, commertypically in the 3 to 5 percent range (See Product Profile, Kemin Foods-L.C., 600 E. Court Ave. Suite A, Des Moines, Iowa 50309). As is seen from the results hereinafter, zeaxanthin to lutein ratios obtained using 'Scarletade' are typically about 4 to about 7 percent, so that these flowers contain up to about 1.25 mg/g zeaxanthin or up to about 0.125 percent dry weight zeaxanthin.

Analysis of lutein esters from fresh marigold petals identified both monoesterified and diesterified lutein. The fatty acid distribution included palmitic, stearic, myristic, oleic, linoleic, lauric, and pentadecanoic [See Gomez et al., *Revista Espanola de Fisiologia* 34:253–256 (1978).]

Moehs et al., *Plant Mol. Biol.*, 45:281–293 (2001) analyzed the biosynthesis of carotenoids in ornamental varieties of *T. erecta*, including a so-called wild type that had dark orange flowers, and plants with yellow, pale yellow and white flowers. Among other findings, those workers reported that although the different plants had a range in flower color from white (mutant) to dark orange, the differences in those flower colors were said to be due to the accumulation of very different amounts of the same carotenoid, lutein, rather than to accumulation of different carotenoid products or intermediates. The differences among the plants studied appeared to relate primarily to regulation of flux through the carotenoid pathway, rather than to the specific type of carotenoid produced or the accumulation of biosynthetic intermediates.

In addition, the so-called wild-type and mutant (white-flowered plant) leaves were reported to contain about the same relative quantity of carotenoid pigments, regardless of flower color. Those pigments were different from the pigments present in the petals. Thus, the only pigment reported for petals was lutein, whereas the leaves were reported to contain lutein as well as β-carotene, violaxanthin and neoxanthin. As is seen from FIG. 1, β-carotene but not lutein can be a precursor to the latter two pigments.

The Moehs et al., authors also compared the *T. erecta* genes they isolated with similar carotenoid-producing genes obtained from the leaves of *Arabidopsis thaliana* (Pogson et al., hereinafter). Identities between the gene products of about 70 to about 80 percent were reported at the protein level, with a higher level if putative plastid targeting signal peptides were excluded, and a lower level of identity at the DNA level. In leaves of *A. thaliana*, lutein is the predominant carotenoid, with β-carotene, violaxanthin and neoxanthin also being formed, but no zeaxanthin being normally accumulated.

Carotenoid biosynthesis in *T. erecta* is a complex system involving many genes and possibly two pathways. The impact of genetic mutations on carotenoid production cannot be predicted a priori. However, classic breeding techniques have produced 'Orangeade", 'Deep Orangeade' and 'Scarletade' *T. erecta* variants that produce the elevated levels of xanthophylls noted above. These relatively recently bred available varieties have not been subject to treatments that induce genetic mutations in an attempt to increase the zeaxanthin ratios.

Several workers have examined the effects of mutagens such as gamma irradiation, ethyl methanesulfonate (EMS) and nitrosomethylurea (NMU) on flowering plants, including marigolds. For example, Zaharia et al., *Buletinul Institutului Agronomic Cluj-Napoca. Seria Agricultura* 44(1): 107–114 (1991) reported on the chlorophyll-deficient effects of carotenoids in the coleoptile after seeds of *Zinnia elegans, Tagetes erecta* and *Callistephus chinensis* were irradiated with gamma irradiation in varying amounts. A paper by Geetha et al., *Acta Botanica Indica*, 20(2):312–314 (1992) reports on the chlorophyll deficient effects of gamma irradiation on *Tagetes patula*.

Diaconu, *Agronomie*, 34(1):17–21 (1991) reported on the effects of EMS on germinating seeds from $F_2$ polycrosses of commonly-called pot marigolds, or *Calendula*, that are not even of the genus *Tagetes*. Those workers noted a wide variation in flower color, inflorescence structure, yield and content of biologically-active substances in $M_2$–$M_4$ plants.

A study by Pogson et al., *Plant Cell*, 8:1627–1639 (1996) used EMS to mutagenize plants of *Arabidopsis thaliana*. This detailed study of 4000 $M_2$ lines reported finding two loci in the carotenoid biosynthetic pathway in leaves that are involved with the production of lutein from γ-carotene. Those loci were referred to as lut1 and lut2. The lut2 locus was reported to be associated with the lycopene ε-ring cyclase enzyme, whereas the lut1 locus was reported to be associated with the lycopene ε-ring hydroxylase. Those workers noted (page 1631) that a decrease in lutein production was compensated for by an equimolar change in the abundance of other carotenoids, although only small amounts of those changes were due to an increased production of zeaxanthin.

Cetl et al., *Folia Fac. Sci. Nat. Univ. Purkynianae Brun Biol.*, 21(1):5–56 (1980) reported extensive studies with *T. erecta* and other *Tagetes* species that from the meager descriptions appeared to all be ornamental varieties. Among those studies, those authors examined the effects of various concentrations of NMU on *T. erecta* seeds, and examined more than about 2000 plants. All $M_2$ plants deviating from the phenotype of the parental cross were recorded, and $M_3$ plants from $M_2$ seeds of the phenotypically different plants were studied.

Those workers assayed plant height, plant diameter, flower head diameter and height of the flower head, as well as time to flowering, branching amount, branch length, cotyledon and leaf size, and flower stalk length. No mention is made regarding flower color or carotenoid levels in the leaves or petals.

Published PCT application WO 00/32788 of DellaPenna et al. asserts of a method of regulating carotenoid biosynthesis in marigolds. Those workers provide polynucleotide sequences said to be those that encode the lycopene β-ring cyclase and lycopene β-ring hydroxylase needed for the preparation of zeaxanthin from lycopene. Also disclosed is a lycopene ε-ring cyclase useful along with the lycopene β-ring cyclase for the preparation of α-carotene from lycopene. No teaching of the lycopene ε-ring hydroxylase needed for lutein production is provided.

Carotenoid biosynthesis is said in PCT application WO 00/32788 to be regulated by expression of a carotenoid synthesizing enzyme-encoding gene already present in marigolds such as those noted above, or by use of an anti-sense RNA encoded by such a nucleotide sequence provided. No evidence of such regulation is provided in the application. The phenomenon known as co-suppression by which the addition of a homologous gene causes both the native gene and transgene not to be expressed is not dealt with by those workers. [See for example, Fray et al., *Plant Mol. Biol.*, 22:589–692 (1993) or Finnegan et al., *Bio/Technology*, 12:883–888 (September 1994).]

In co-owned PCT application PCT/US02/20633 and related application Ser. No. 10/180,775 and its continuation-in-part application Ser. No. 10/325,265, the inventors describe mutant marigold plants that provide flower petals containing a commercially useful amount of zeaxanthin esters. The plants have an altered ratio of lutein and zeaxanthin such that the usually reported 4 to about 7 percent zeaxanthin level is raised and the amount of lutein is decreased. The above-noted applications and co-owned PCT application describe such marigold plants, whereas the present invention contemplates a concentrated marigold plant extract that is preferably obtained from such a plant, and formulated to provide mixed zeaxanthin esters in an amount useful to prevent cancer, or to treat or prevent cataract formation, macular degeneration or a free radical-mediated disease.

BRIEF SUMMARY OF THE INVENTION

The present invention contemplates mixed zeaxanthin esters and more particularly a purified carotenoid concentrate comprising mixed zeaxanthin esters, as well as various mixed zeaxanthin ester compositions that can be prepared from that concentrate. A contemplated purified concentrate is a solid to semi-solid that includes mixed zeaxanthin esters at about 50 milligrams per gram or more of the concentrate with zeaxanthin at about 20 percent or more of the total carotenoids present when assayed after saponification. In a preferred embodiment, the zeaxanthin is about 25 percent or more of the total carotenoids present when assayed after saponification. In some embodiments, the concentrate includes at least one additional carotenoid in free or esterified form. In a preferred embodiment, the mixed zeaxanthin esters are extracted from the species *Tagetes erecta*.

Another aspect of the invention contemplates a diluted, purified carotenoid composition comprising mixed zeaxanthin esters dissolved or dispersed in a comestible diluent. Such a contemplated composition can be prepared using the above described concentrate and includes mixed zeaxanthin esters at about 10 milligrams per gram or more of the diluted composition with the zeaxanthin at about 20 percent or more of the total carotenoids present when assayed after saponification. In one preferred embodiment, the diluent is an oil.

In another embodiment, the composition is present encapsulated in a beadlet. In another preferred embodiment, the zeaxanthin is about 25 percent or more of the total carotenoids present when assayed after saponification. In some embodiments, the composition includes at least one additional carotenoid in free or esterified form. In a preferred embodiment, the mixed zeaxanthin esters are extracted from the species *Tagetes erecta*.

One contemplated use of this aspect of the invention is a nutritionally effective amount of the mixed zeaxanthin esters in a unit dosage form suitable for oral administration such as packets, tablets, capsules, and powders in vials or ampules. Such a nutritionally effective amount can be an amount that is sufficient to prevent cancer, or to treat or prevent cataract formation, macular degeneration or a free radical-mediated disease. In a preferred embodiment, the composition contains about 2 milligrams or more of mixed zeaxanthin esters.

Another contemplated use of this aspect of the invention includes a nutritionally effective amount of the mixed zeaxanthin esters as an additive in a food substance or beverage. The food substance can include items processed for human consumption as well as pet foods. The incorporated nutritionally effective amount can be an amount that is sufficient to prevent cancer, or to treat or prevent cataract formation, macular degeneration or a free radical-mediated disease. In some embodiments, the food substance or beverage contains about 0.5 milligram or more mixed zeaxanthin esters per serving. In a preferred embodiment, the food is a medical food having a dosage that does not exceed 40 mg per day.

Another aspect of the invention contemplates a diluted, purified carotenoid composition comprising mixed zeaxanthin esters dissolved or dispersed in a cosmetically acceptable diluent. Such a contemplated composition can be prepared using the previously described concentrate and includes mixed zeaxanthin esters at about 10 milligrams per gram or more of the diluted composition with the zeaxanthin at about 20 percent or more of the total carotenoids present when assayed after saponification. In a preferred embodiment, the zeaxanthin is about 25 percent or more of the total carotenoids present when assayed after saponification. In some embodiments, the composition includes at least one additional carotenoid in free or esterified form. In a preferred embodiment, the mixed zeaxanthin esters are extracted from the species *Tagetes erecta*. A contemplated use of this aspect of the invention includes a light protective amount of the mixed zeaxanthin esters contained in a cream, lotion, or ointment adapted for topical application to human skin.

The present invention has several benefits and advantages.

One benefit of the invention is that large quantities of mixed zeaxanthin esters can now be economically provided in purified concentrated form.

An advantage of the invention is that food supplements comprising a nutritionally effective amount of mixed zeaxanthin esters and an optional one or more carotenoid are now available.

Another benefit of the invention is the provision of a food substance or beverage that contains a nutritionally effective amount of the mixed zeaxanthin esters.

A further advantage of the invention is the provision of a medical food containing an amount of mixed zeaxanthin esters sufficient to prevent free radical-mediated diseases.

Yet a further benefit of the invention is the provision of a topical cream, lotion or ointment that contains a light protective amount of mixed zeaxanthin esters.

Still further benefits and advantages will be apparent to the reader from the detailed description that follows.

BRIEF DESCRIPTION OF THE DRAWING

In the drawing forming a part of this disclosure.

Figure 1:
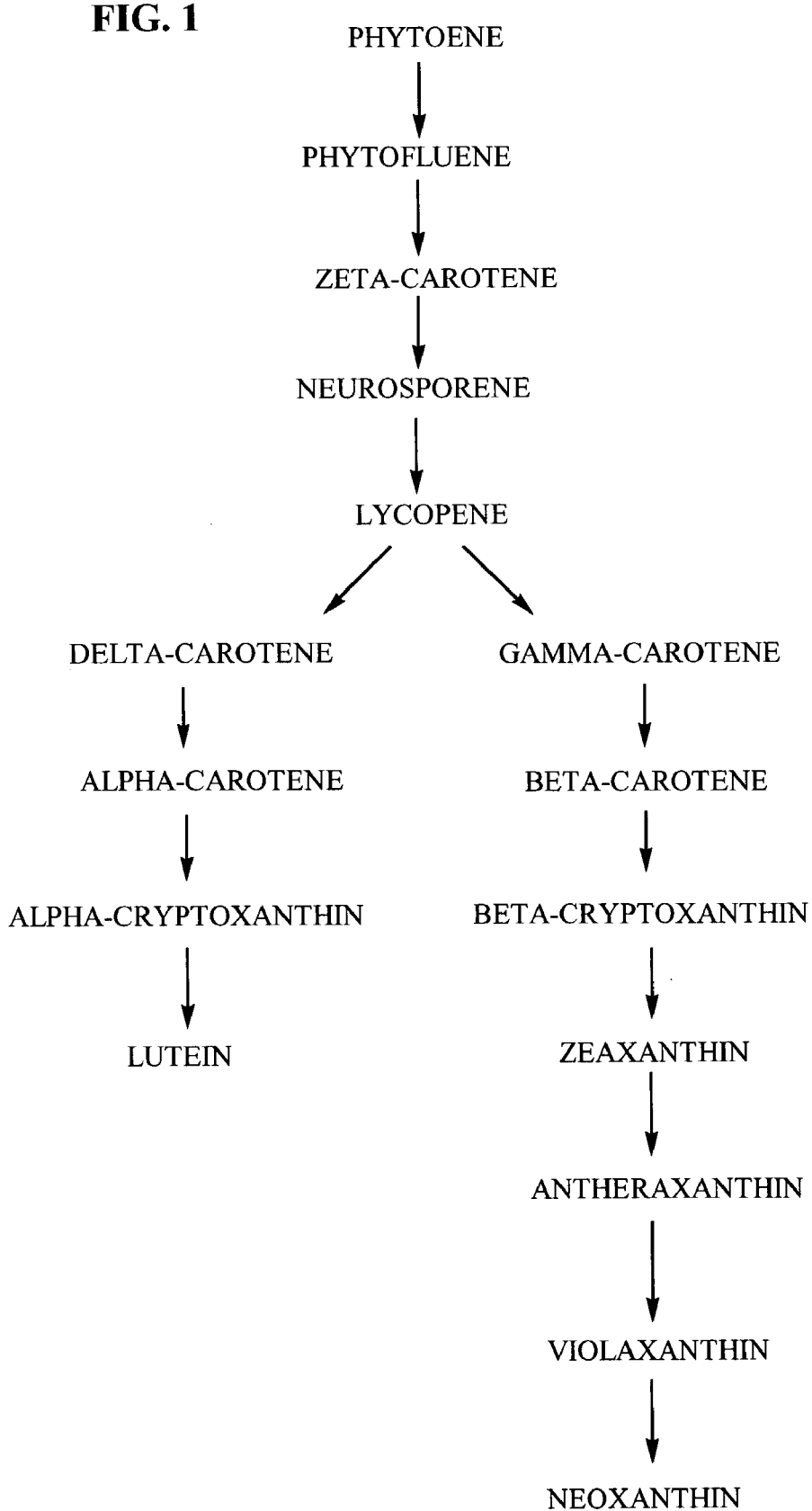
FIG. 1 is a schematic representation of the biological synthesis pathway for the production of lutein and zeaxanthin in plants in which phytoene, the first $C_{40}$ carotenoid in the pathway, is converted in several steps (four arrows) through zeta-carotene ($\zeta$-carotene) to lycopene, after which the pathway splits to form $\delta$-carotene that contains one $\epsilon$-ring, then $\alpha$-carotene that contains one $\epsilon$-ring and one $\beta$-ring or to form $\gamma$-carotene that contains one $\beta$-ring, then $\beta$-carotene that contains two $\beta$-rings, and after several steps, to lutein or zeaxanthin, respectively, and the zeaxanthin branch continuing to the epoxide-containing xanthophylls antheraxanthin, violaxanthin and neoxanthin.

As used herein, the term "zeaxanthin ratio" is defined as the quantity of zeaxanthin present in a dried flower petal or leaf divided by the quantity of zeaxanthin plus lutein [zeaxanthin/(lutein+zeaxanthin)] present in that petal or leaf. The "neoxanthin plus violaxanthin ratio" is similarly calculated as the ratio of neoxanthin+violaxanthin divided by the sum of those two pigments plus lutein. The "$\beta$-carotene ratio", the "lycopene ratio", the "$\alpha$-cryptoxanthin ratio", the "phytoene ratio" and the "phytofluene ratio" are similarly calculated using the named pigment amount as the sum of its isomers as the numerator and the sum of that pigment plus lutein as the denominator. The sums of appropriate percentages can also be used for those calculations. Those pigment quantities are determined by high performance liquid chromatography (HPLC) after saponification of a dried flower petal or leaf extract as discussed hereinafter so that the amount of each of lutein and zeaxanthin (or other pigment) is measured in the free compound form, e.g., alcohol form for lutein and zeaxanthin, present after saponification rather than in the esterified form that is present in the fresh flower petal, and chlorophyll that can be present in a leaf extract is destroyed. Some of the flower petals and leaves of plants discussed herein contain very low or unmeasurable amounts of lutein or lutein esters, e.g., less than about 0.1–0.2 percent. When that is the case, the amount of lutein in the denominator of a ratio approaches zero and the ratio approaches one.

The word "oleoresin" is used herein to mean an extract of plant tissues that contains plant pigments such as the xanthophylls discussed herein in their esterified forms, sometimes accompanied by amounts of other plant products and pigments such as other carotenoids such as $\beta$-carotene, as well as small amounts of solvent such as hexane or acetone, typically less than 1 percent organic solvent. Xanthophylls are typically present as mono- or diesters in flower petals and are typically present as free alcohols in marigold leaves. Carotenes such as $\beta$-carotene or lycopene are present as free, non-chemically-combined compounds. Chlorophyll is present in marigold leaves and largely absent in the petals. Thus, an oleoresin prepared from flower petals contains xanthophyll esters and/or hydrocarbon carotenes and is largely free of chlorophyll, whereas an oleoresin prepared from marigold leaves contains chlorophyll and free xanthophylls and carotenes. An oleoresin is a solid or semi-solid material.

DETAILED DESCRIPTION OF THE INVENTION

The present invention contemplates mixed zeaxanthin esters in the form of a concentrate, and the several uses to which such a concentrate can be put as well as the several products that can be prepared therefrom. As will be discussed in greater detail hereinafter, a contemplated concentrate is typically an extract of plant tissues such as the petals of a flower such as the preferred marigolds, Tagetes erecta. Dried flower petals typically contain about 0.2 to 0.3 percent mixed zeaxanthin esters, whereas dried petals contemplated herein contain about 0.4 to about 1.2 percent mixed zeaxanthin esters. A first plant extract is referred to in the art as an oleoresin and contains about 10 times more than the dried source plant tissue of the desired mixed zeaxanthin esters as well as other plant materials. A contemplated concentrate results from purification of an oleoresin and contains at least 40 times more of the desired mixed zeaxanthin esters per weight than the dried source plant tissue.

A contemplated concentrate is typically in the form of a solid or semi-solid that can have the consistency of a gum. The differences in physical form are largely due to the constituents present, with more constituents usually leading to a softer, less solid material.

The zeaxanthin esters can be present as multiple diesters, multiple monoesters or mixtures of both diesters and monoesters. Zeaxanthin is a dialcohol (diol) and therefore can be singly or doubly esterified. The acids from which the mono- and diesters of zeaxanthin are formed are the fatty acids naturally found in plants, and particularly in flower petals. Illustrative plant fatty acids contain 8 to about 20 carbon atoms in a straight chain with zero to about three ethylenic unsaturations per molecule. Such illustrative fatty acids include lauric, myristic, palmitic, stearic, palmitoleic, oleic, linoleic, pentadecanoic, capric, and linolenic acids. Typical fatty acids include palmitic, stearic, myristic, oleic, linoleic, lauric, and pentadecanoic acids. The zeaxanthin esters of a contemplated concentrate are a mixture that contains two or more zeaxanthin esters of the above carboxylic acids, with the particular carboxylic acids present being a function of the plant and plant part from which the esters were obtained. The mixture can contain single zeaxanthin molecule portions esterified with different, mixed carboxylic acids or a mixture of zeaxanthin ester molecules each of which contains two of the same carboxylic acid portions, with different zeaxanthin ester molecules containing different carboxylic acid portions.

The mass contributed by the carboxylic acids of the diesters is about one-half the mass of a diester molecule, and about one-third the mass of a monoester. However, for convenience, the amount of zeaxanthin present in a contemplated concentrate or other zeaxanthin ester-containing composition discussed herein is determined as zeaxanthin itself, in the free dialcohol (diol) form following hydrolysis or saponification of a sample to be assayed using HPLC as is discussed hereinafter. When a contemplated concentrate is assayed after saponification, the zeaxanthin can be about 20 percent or more of the total carotenoids present. In another embodiment, the zeaxanthin can be about 25 percent or more of the total carotenoids present after saponification. In a preferred embodiment, the zeaxanthin is about 30 percent or more of the total carotenoids present after saponification.

Carotenoids in general, and specific carotenoids such as the carotenes, phytoene and lycopene, and the xanthophylls such as lutein and zeaxanthin, are known to have antioxidant properties and provide associated health benefits. Including at least one additional carotenoid either in free or esterified form in the contemplated concentrate or the diluted products derived from it can provide enhanced health benefits in the consumer formulated products. The additional carotenoid can be a carotene, a xanthophyll, a monoesterified xanthophyll, a diesterified xanthophyll or mixtures thereof. Examples of carotenes include phytoene, phytofluene, ζ-carotene, neurosporene, lycopene, δ-carotene, α-carotene, γ-carotene, and β-carotene. Xanthophyll examples include α-cryptoxanthin, lutein, β-crytoxanthin, zeaxanthin, antheraxanthin, violaxanthin, and neoxanthin. The carboxylic acid portion of a xanthophyll ester or diester also present admixed with the zeaxanthin ester or diester is selected from the before-mentioned carboxylic acids that can provide the carboxylic acid portion of a zeaxanthin ester or diester.

A contemplated purified concentrate comprising mixed zeaxanthin esters is typically produced from an oleoresin. As is well known in the art, an oleoresin is a solid extract of plant tissues that contains plant pigments such as lutein and zeaxanthin in esterified forms. The pigments are sometimes accompanied by other plant products and pigments such as other xanthophyll esters or carotenes, as well as small amounts of the extracting solvent such as hexane or acetone. Preferably, the oleoresin is extracted from the flowers of the marigold, Tagetes erecta, and contains fatty acid esters and free carotenoids as are present in the flowers of a plant. Oleoresins are items of commerce and are sold to processors for further treatment in the production of human or other animal food supplements.

In an illustrative marigold concentrate preparation, mixed zeaxanthin esters and possibly other xanthophyll esters or carotenes, are extracted from dried, usually comminuted, marigold flower petals using hexane, acetone, ethyl acetate or the like organic solvent as the extractant. The extraction is carried out according to procedures known in the art. The solvent(s) is removed, typically under vacuum, resulting in an extract referred to as an oleoresin that contains a high level of xanthophyll esters and is about 99 percent and preferably about 99.9 percent free of the extracting organic solvent; i.e., contains less than about 1 percent and preferably less than about 0.1 percent organic solvent by weight. The oleoresin can be further purified in a low molecular weight alcohol to separate non-xanthophyll lipids or residues of pesticides. It is then concentrated under vacuum to yield a sufficiently high concentration suitable for direct use in supplement formulations, topical applications, or as food additives. The concentrate described above can also be diluted to form products, such as an oil solution or encapsulated in a beadlet, to be sold for use in supplement formulations, topical applications, or as food additives.

The concentrate is a dark orange-brown solid or semi-solid such as a gum containing mixed zeaxanthin esters as can be measured using spectrophotometry. Concentrates are dissolved in hexane and measured at a wavelength of maximum absorption of approximately 450 nm for zeaxanthin esters using the 1 percent extinction coefficient e of 1260. [See Levy U.S. Pat. No. 6,191,293.]. A contemplated purified concentrate includes mixed zeaxanthin esters with the zeaxanthin at about 20 percent or more of the total carotenoids present when assayed after saponification.

Purification methods useful in the preparation of a contemplated concentrate as by dissolution and filtration are adapted from analogous procedures known in the art. Tyczkowski et al. developed simple extraction and crystallization procedures that gave lutein of 96.0 to 99.2 percent purity from commercially available saponified extracts of marigold. Lutein esters were synthetically prepared to provide compounds useful for laboratory scale processes. [See Tyczkowski et al., Poultry Science 70:651–654 (1990).] In U.S. Pat. No. 4,048,203, Philip describes the extraction of lutein esters from plant material, and further purification of the esters using alcohol at 75° C. In U.S. Pat. No. 5,382,714, Khachik describes a process for the isolation, purification, and recrystallization of lutein from saponified marigold oleoresin, and in U.S. Pat. No. 5,648,564 Ausich et al. describes a process for the extraction, isolation, and purification of comestible xanthophyll crystals from plants. Both of these latter processes require a saponification step, whereby the natural xanthophyll ester form present in the plant material is destroyed.

Schulz, in U.S. Pat. No. 4,105,855, teaches a method for synthesizing symmetrical carotenoids, which can be esters.

The only ester of zeaxanthin mentioned by Schulz is the diacetate as a last intermediate step in obtaining the diol. Schulz does not teach the synthesis or extraction of mixed zeaxanthin esters or their concentrates.

In U.S. Pat. No. 6,191,293, Levy illustrates a xanthophyll ester preparation from Chinese wolfberries, *Lycium chinense*. Other researchers show that *L. chinense* has a single diester, zeaxanthin dipalmiate [See Kim et al., *Arch. Pharm. Res.*, 20(6):529–532 (1997).] The method described in that patent is nonetheless useful herein for obtaining the desired mixed zeaxanthin ester concentrate.

An industrial process to obtain xanthophyll concentrates of high purity is described by Montoya-Olvera et al. in U.S. Pat. No. 6,504,067. Impurities including free fatty acids, gums, waxes, phoshatides, lipids, sterols, chlorophylls and volatile compounds are eliminated or removed in different stages, while the xanthophylls concentrate is enriched after each stage. Using this process, saponified concentrates of over 90 percent purity are prepared from plant extracts including marigold oleoresin.

A purified concentrate of mixed zeaxanthin esters can be dissolved or dispersed in an appropriate comestible diluent such as an edible vegetable oil, pectin, or dry starch to produce a diluted composition and includes the mixed zeaxanthin esters at about 5 milligrams per gram of the diluted composition. When a contemplated composition is assayed after saponification, the zeaxanthin is about 20 percent or more of the total carotenoids present. In a preferred embodiment, the zeaxanthin is about 25 percent or more of the total carotenoids present when assayed after saponification.

Exemplary oils include candelilia, coconut, cod liver, cottonseed, menhaden, olive, palm, corn, soybean, peanut, poppy seed, safflower and sunflower oil. The use of an oil having a relatively high concentration of unsaturated fatty acids is preferred; i.e., the use of an oil having an iodine value of about 100–150 is preferred. Herring oil, corn oil, cottonseed oil, mustard oil, poppy seed oil, rape seed oil, safflower oil, sesame oil, soybean oil, sunflower oil, and wheat germ oil are illustrative of such oils.

A purified concentrate of mixed zeaxanthin esters can be dissolved or dispersed in an appropriate cosmetically acceptable diluent and includes the mixed zeaxanthin esters at about 5 milligrams per gram of the diluted composition. The diluent selected can be solid, liquid or a semi-solid such as petrolatum to produce a diluted composition. The diluted, purified mixed zeaxanthin ester product so produced can be a dispersion such as a solid-in-solid dispersion, an emulsion such as an oil-in-water or water-in-oil emulsion or a solution as where an appropriate oil as discussed elsewhere is the diluent. When a contemplated composition is assayed after saponification, the zeaxanthin can be about 20 percent or more of the total carotenoids present. In a preferred embodiment, the zeaxanthin is about 25 percent or more of the total carotenoids present when assayed after saponification.

Additional acceptable diluents include cocoa butter, dicalcium phosphate, calcium sulfate, lactose, cellulose, kaolin, mannitol, dry starch, powdered sugar, sorbitol and inositol. For emulsion-type compositions, emulsifying agents can be natural or synthetic and can include gelatin, egg yolk, casein, pectin, sodium lauryl sulfate, polyethylene glycol 400 monostearate, bentonite, and magnesium trisilicate. Additional comestible and cosmetically acceptable diluents are noted in such references as *Remington's Pharmaceutical Sciences* Eighteenth Edition, Gennaro ed., Mack Publishing 1990 and *Handbook of Pharmaceutical Excipients*, Rowe et al. eds., Pharmaceutical Press 2003.

To produce one diluted product, an admixture of oil and the concentrate containing mixed zeaxanthin esters is typically carried out using a mixing apparatus, as is well known.

Additives such as α-tocopherol, can also be present as is noted in Khachik U.S. Pat. No. 5,382,714 for preventing possible oxidation during long term storage.

The diluted purified carotenoid composition comprising mixed zeaxanthin esters can also be present encapsulated within generally spherical small pellets that are conventionally referred to as "beadlets". Exemplary beadlets are water-insoluble and are prepared by encapsulation of the diluted carotenoid composition of mixed zeaxanthin esters by cross-linked gelatin as is disclosed in U.S. Pat. No. 4,670,247 or an alginate such as sodium alginate as is disclosed in U.S. Pat. No. 6,150,086.

Using cross-linked gelatin as illustrative, a water-insoluble beadlet is prepared by forming an emulsion containing the mixed zeaxanthin esters, water, gelatin, and a sugar. The emulsion is converted into droplets that are individually collected in a mass of starchy powder in such a manner that the particles from the droplets are kept separated from each other until their particulate form is permanently established. The carotenoid-containing particles are separated from the starchy collecting powder, and heat-treated at a temperature of about 90° C. to about 180° C. The heat treatment step insolubilizes the gelatin matrix of the beadlet by a reaction between the carbonyl group of the sugar with the free amino moieties of the gelatin molecule. The resulting beadlets are water-insoluble and exhibit increased stability to the stresses of feed pelleting. The cross-linking process utilizes the ingredients employed in making the beadlet and does not require addition of a cross-linking reagent or additive to the composition.

U.S. Pat. No. 5,695,794 discloses another form of beadlets that can be adapted for use herein. Here, beadlets having diameters of about 30 to about 55 microns are prepared by spraying a molten solution of a desired amount of mixed zeaxanthin esters in hydrogenated vegetable oil such as hydrogenated cotton seed oil, wheat-germ oil, safflower oil, soybean oil and the like, that also can contain mono- and diglycerides such as those prepared from hydrogenated soybean mono- and diglycerides, cottonseed mono- and diglycerides and the like, as well as citric acid and 2,6-di-tert-butyl-4-methylphenol (BHT) as antioxidants. Other antioxidants such as ethoxiquin, vitamin E and the like can also be used, as is well known. The molten mixture is sprayed at a temperature of about 160° F. (about 70° C.) into a cyclonic air stream of a spray chiller such as available from Niro, Inc., Columbia, Md. to produce the beadlets that solidify on cooling. The cooled beadlets are dusted with an anticaking agent such as fumed silica, calcium phosphate, powdered starch or cellulose as are well known to form the beadlets that are preferably added to the feed as supplement.

A contemplated purified concentrate comprising mixed zeaxanthin esters can also be produced from synthetically derived zeaxanthin esters. Sources for zeaxanthin include organic synthesis, as well as naturally occurring and genetically modified organisms. In U.S. Pat. No. 6,150,561, Kreienbuhl et al. describes the synthetic production of zeaxanthin using a Wittig reaction. Synthetic zeaxanthin is commercially available from Roche Vitamins, Inc. In U.S. Pat. No. 5,747,544, Garnett et al. describes zeaxanthin preparations containing the desired 3R, 3'R isomer produced by fermentation of *Flavobacterium multivorum* cells, as well as from other host cells containing genes isolated from this *F. multivorum* strain.

Genes that encode enzymes that transform ubiquitous precursors such as geranyl pyrophosphate and farnesyl pyrophosphate into geranylgeranyl pyrophosphate (GGPP), and GGPP into beta-carotene are of importance in producing genetically modified organisms that produce zeaxanthin. Ausich et al. U.S. Pat. No. 5,684,238, discloses appropriate methods, *E. herbicola* nucleic acid sequences and deposited

*E. herbicola* DNA-containing cells for the formation of GGPP and the conversion of GGPP into phytoene, phytoene into lycopene and lycopene into beta-carotene in a transformed host plant. That patent also teaches methods, *E. herbicola* nucleic acid sequences and deposited *E. herbicola* DNA-containing cells for the conversion of beta-carotene into zeaxanthin in a host organism. Transformation of a host organism to express each of those genes, each gene encoding a chimeric enzyme containing an N-terminal transit peptide sequence, provides a transgenic organism that produces zeaxanthin esters. It is also to be understood that a DNA sequence of an appropriate gene from *E. uredovora* [Misawa et al., U.S. Pat. No. 5,429,939] or a variant that encodes a chimeric enzyme having an N-terminal plastid transit peptide can be used in place of a DNA sequence from *E. herbicola*.

The zeaxanthin produced from a source described above can be then esterified with mixed $C_8$–$C_{20}$ carboxylic acid chlorides followed by recovery of mixed zeaxanthin esters similar to the esters isolated from marigold plants. However, such a chemically-synthesized preparation would be more costly than a concentrate produced from marigolds as previously described. Not only is the chemical synthesis of ester products costly, but so too is the preparation of the zeaxanthin, be it synthetic or from fermentation of an organism. In addition, the synthetic zeaxanthin process yields biologically inactive isomers that should be separated from the desired 3R, 3'R isomer. Although expensive, such derived mixed zeaxanthin esters can be admixed with the carotenoid concentrate described herein before or used instead of that concentrate.

One contemplated use of the purified concentrate or diluted compositions of the mixed zeaxanthin esters is in a composition that is adapted for oral administration and is intended and well-suited for introduction into a mammalian host, such as a human. The mixed zeaxanthin esters can be derived from a marigold extract as well as the previously noted synthetically derived esters. A contemplated composition for oral administration can be prepared using the mixed zeaxanthin ester active agent in accordance with conventional food supplement or pharmaceutical practice. The diluents, excipients, or carriers that can be used are well known for such formulations, and the form chosen depends on the given context.

Preferably, the composition suitable for oral administration is in unit dosage form. In such form, the composition is divided into unit doses containing appropriate quantities of the mixed zeaxanthin esters. The unit dosage form can be a packaged preparation, the package containing discrete quantities of the preparation, for example, packets, tablets, capsules, and powders in vials or ampules. The unit dosage form can also be a capsule, cachet, or tablet itself, or it can be the appropriate number of any of these packaged forms.

In some embodiments, the contemplated composition is used in a nutritionally effective unit dosage form in an amount effective for preventing cancer, or for treating or preventing cataract formation, macular degeneration or a free radical-mediated disease. The term "nutritionally effective amount" is used herein to mean an amount of mixed zeaxanthin esters which, when administered, achieves the desired preventative or treatment effect. Typically, a nutritionally effective amount is in the range of 0.5 mg per serving with a maximum dosage that typically does not exceed 40 mg/day. In a preferred embodiment, the composition provides 2 milligrams or more of mixed zeaxanthin esters in a unit dosage form.

Another contemplated use of the mixed zeaxanthin esters is as an additive in food preparations such as baked goods and baking mixes, soy milk, beverages and beverage powders, frozen dairy desserts and mixes, processed fruit and vegetable products, egg products and egg substitutes, breakfast cereals, fats and oils, hard candy, fruit snacks, dairy products, syrups, meat preparations including pet foods and other similar foodstuffs that are not be subjected to harsh cooking conditions [e.g., temperatures of more than about 400° F., about 205° C.].

When consumed by humans or other mammals, the mixed zeaxanthin esters, of the contemplated composition are used in an amount to prevent cancer, or to treat or prevent cataract formation, macular degeneration or free radical-mediated diseases. In a preferred embodiment, the contemplated food substance or beverage provides about 0.5 milligrams to about 8 milligrams of mixed zeaxanthin esters per serving. In a more preferred embodiment, the contemplated food substance or beverage provides about 2 milligrams to about 6 milligrams of mixed zeaxanthin esters per serving.

Another contemplated use of the purified concentrate or diluted compositions of the mixed zeaxanthin esters is in medical foods intended as the sole item of the diet. A medical food is defined by the Orphan Drug Act as a food that is formulated to be consumed or administered orally under the supervision of a physician and that is intended for the dietary management of a disease or condition for which distinctive nutritional requirements, based on recognized scientific principles, are established by medical evaluation. In some embodiments, the contemplated composition is used in an amount to prevent cancer, or to treat or prevent cataract formation, macular degeneration or free radical-mediated diseases. In a preferred embodiment, the medical food provides up to about 40 milligrams of mixed zeaxanthin esters per day. In a more preferred embodiment, the medical food provides about 30 milligrams to about 40 milligrams mixed zeaxanthin esters per day.

Mixed zeaxanthin esters possess antioxidant properties and absorb blue light as well as a portion in the ultra violet (UV) light region making them effective in preventing damage that results from exposure to harmful irradiation. The 320 to 400 nanometer wavelength ultraviolet radiation range is designated by the cosmetic industry as being the "UVA" wavelength range and is known to produce inflammation or blistering of the skin (i.e., sunburn). In addition to the short-term hazard caused by sunlight, there are also long-term hazards associated with this UV radiation exposure. One of these long-term hazards is malignant change in the skin surface. Numerous epidemiologic studies have been conducted whose results demonstrate a strong relationship between sunlight exposure and human skin cancer. Another long-term hazard of ultraviolet radiation is premature aging of the skin.

When a contemplated preparation is used on skin, damage to be mitigated or prevented can be any skin damage such as burns, blisters, or damage appearing after chronic exposure to sun, e.g. premature aging of the skin. Exact amounts of protection vary depending upon the Sun Protection Factor (SPF). SPF is a commonly used measure of photoprotection of a sunscreen. Sunscreen compositions comprising mixtures of molecules that absorb at different UV wavelengths and thereby protect the skin are known in the art. [See Haffey et al. U.S. Pat. No. 5,087,445 and Turner et al. U.S. Pat. No. 5,073,372.]

In one embodiment of the invention, a light protection effective amount of the mixed zeaxanthin esters are dissolved or dispersed in a diluent for use as a topical cream or lotion. The term "light protection effective amount" is used herein to mean an amount of mixed zeaxanthin esters which, when administered, achieves the desired protective effect. A topical cream, lotion, or ointment can be in the form of a gel, an oil-in-water or water-in-oil emulsion, or a salve. In one preferred embodiment, the light protective amount of the mixed zeaxanthin esters is about 0.5 to about 20 percent weight of the topical cream, lotion, or ointment and more preferably 5 to 15 percent weight of the topical cream, lotion or ointment.

Petals from the flowers of a plant of the family Compositae, and in particular, a plant of the species *Tagetes erecta*, marigold are extracted commercially to supply lutein esters formulated into 10 percent beadlets and 15 percent oil suspensions. In those commercial formulations, zeaxanthin esters are a minor constituent. Analysis of a 15 percent lutein ester oil suspension, after hydrolysis, identified lutein at 75.7 milligrams per gram, zeaxanthin at 3.9 milligrams per gram and crytoxanthin at 0.4 milligrams per gram. [See Cognis Corp. web site at cognis.com].

Although not at commercially feasible levels for extraction, zeaxanthin esters have been identified in other sources including tangerine, potato, red pepper, persimmon and peaches. Tangerine juice has been shown to contain 37.6 mmol/g zeaxanthin esters and persimmon fruit has been shown to contain 8.57 µg/g zeaxanthin esters. [See Wingerath et al., *J. Agric. Food Chem.*, 44:2006–2013 (1996); Breithaupt et al., *J. Agric. Food Chem.* 50:7175–7181 (2002); Breithaupt et al., *Eur. Food Res. Technol.*, 211: 52–55 (2000); Philip et al., *J. Food Sci.*, 53(6): 1720–1722, and 1745 (1988); and Khachik et al., *J. Agric. Food Chem.*, 37(6):1465–1473 (1989).] Data from the above Wingerath et al. paper indicate that fatty acid esters of $\beta$-cryptoxanthin predominate over similar esters of zeaxanthin in a concentrate prepared from tangerines and that $\beta$-cryptoxanthin predominates over zeaxanthin after saponification of the concentrate, whereas the data in Tables 6 and 7 herein indicate that zeaxanthin predominates over $\beta$-cryptoxanthin after saponification in a contemplated concentrate prepared from marigolds. That Wingerath et al. paper also indicates that only free, unesterified zeaxanthin and $\beta$-cryptoxanthin are present in a concentrate prepared from orange juice. The above Philip et al. paper similarly provides data showing $\beta$-cryptoxanthin esters being in excess over zeaxanthin esters present in a concentrate prepared from persimmons.

Currently available marigolds are not suitable for the commercial extraction of mixed zeaxanthin esters due to the low quantities present in the flowers. However, a marigold having an altered carotenoid profile can be used to provide the mixed zeaxanthin esters in a concentrate or diluted compositions. Plants having altered carotenoid profiles can be produced through various methods of mutagenesis or by genetic engineering to form a transgenic plant as is disclosed in the before-noted co-owned patent applications.

Mutagenic agents useful for altering plants are well known in the art, as are methods of using such agents. Exemplary chemical mutagens include nitrosomethylurea (NMU), ethyl methanesulfonate (EMS), methyl methanesulfonate, diethyl sulfate, nitrosoguanidine, and ethylnitrosourea of which EMS is preferred herein. NMU can be used as discussed in Cetl et al., *Folia Fac. Sci. Nat. Univ. Purkynianae Brun. Biol.*, 21(1):5–56 (1980), whereas EMS is typically utilized at about 0.25 to about 1 percent by volume (v/v), and preferably at about 0.2 to about 0.8 percent.

In addition to chemical mutants, plants can be mutated to effect alterations in carotenoid profiles using ionizing radiation as by gamma rays or neutrons. Gamma rays and fast neutron bombardment have been used for other plants to cause deletions of one or more genes. Gamma irradiation is a useful mutagenic agent when used to irradiate seeds at a dose of 200 to about 20,000 rads (0.2 to about 20 krads). Still further techniques are well known to workers skilled in this art. Such mutated plants can be thus referred to as chemically-induced, or ionizing radiation-induced, respectively. As a consequence, a mutant host plant such as a marigold is defined herein as a marigold plant obtained by chemically-induced mutation or ionizing radiation-induced mutation.

Regardless of the mutagen used, the phenotype of most of the resulting mutant plants, including carotenoid-related traits such as the zeaxanthin ratio and the amount of xanthophylls in the petals, is usually substantially identical to that of the parent, so that a very large percentage of the mutants obtained are not useful. In addition, plants seeming to have the same phenotype as the parent need to be screened to locate a desired mutant plant. Those screenings, although tedious, are routinely carried out and involve analysis of carotenoid pigments from one or more single flower petals or leaves or both. Thus, the preparation of a desired mutant is a relatively rare, but repeatable event. For example, in one study herein, only twenty-three useful mutants were obtained from almost 22,000 mutant plants examined that had zeaxanthin ratios of about 1:10 or more, and only two plants out of those twenty-three had zeaxanthin ratios greater than about 9:1. In another study, about 43 mutants out of about 8200 examined plants exhibited zeaxanthin ratios of about 1:10 or greater.

A marigold plant that can be the source material of mixed zeaxanthin esters can be a plant that grows from the seed of a selfing or cross of an identified mutagenized plant. The source marigold plant can be a hybrid formed by crossing the flowers of two plants that arose from two different mutagenized plants from independent $M_1$ plants ($M_1 \times M_1$). It can also be a hybrid formed by crossing the flowers of one plant that arose from one mutagenized plant with a non-mutagenized plant, or a hybrid formed by back-crossing a hybrid with one or the other of its immediate parental flowers. In addition, two different hybrid plants can be crossed or a hybrid can be selfed. The produced plants are screened and selected for desired carotenoid characteristics.

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

EXAMPLE 1

EMS Treatment of *Tagetes erecta* 'Scarletade'

Seeds of *Tagetes erecta* xanthophyll marigold denominated 'Scarletade' (commercially available from PanAmerican Seed Co. 622 Town Road, West Chicago, Ill. 60185) were treated with ethyl methanesulfonate (EMS, commercially available from Sigma Chemical Co., St. Louis, Mo. 63178). Approximately 2,500 seeds were added to 400 ml of 0.4% (v/v) or 0.8% (v/v) EMS and were stirred gently for eight hours at ambient temperature. During a four-hour period following the EMS treatment, the seeds were washed sixteen times, each wash using continuous stirring with 400 ml distilled water. The treated seeds, identified as $M_1$ seeds, were then sown in trays containing soilless potting mix.

After several weeks, the seedlings were transplanted into pots containing soilless potting mix and maintained in the greenhouse. Flowers produced by those plants were naturally self-pollinated. The resulting seeds, identified as $M_2$ seeds, were harvested from approximately 2,300 plants. Of these 2,300 plants, approximately 1,500 were grown from seeds treated with 0.4% EMS and approximately 800 were grown from seeds treated with 0.8% EMS. To facilitate identification of mutant plants, the $M_2$ seeds from each of 50 $M_1$ plants were combined into one lot, resulting in a total of 47 seed lots. During the summer of the year 2000, 500 seeds from each of the 47 lots were sown and the resulting plants were field-grown at PanAmerican Seed Co. in Santa Paula, Calif. 93060.

EXAMPLE 2

HPLC Screening of EMS-Treated *Tagetes erecta* 'Scarletade'

EMS-treated 'Scarletade' plants were field-grown at PanAmerican Seed Co. in Santa Paula, Calif. 93060, and were screened by HPLC for altered zeaxanthin ratio. Flowers approximately 98% fully opened were selected for analysis. From each flower, one petal was removed one-third of the distance from the flower center and placed in a 3.5"×0.75" glass vial containing approximately 5 grams of glass beads. Vials were packaged with dry ice until stored at −80° C.

For analysis, solvent delivery and aliquot removal were accomplished with a robotic system comprising a single injector valve Gilson 232XL and a 402 2S1V diluter [Gilson, Inc. USA, 3000 W. Beltline Highway, Middleton, Wis.]. For saponification, 3 ml of 50% potassium hydroxide hydroethanolic solution (4 water:1 ethanol) was added to each vial, followed by the addition of 3 ml of octanol. The saponification treatment was conducted at room temperature with vials maintained on an IKA HS 501 horizontal shaker [Labworld-online, Inc. Wilmington, N.C.] for fifteen hours at 250 movements/minute, followed by a stationary phase of approximately one hour.

Following saponification, the supernatant was diluted with 0.9 ml of methanol. The addition of methanol was conducted under pressure to ensure sample homogeneity. Using a 0.25 ml syringe, a 0.1 ml aliquot was removed and transferred to HPLC vials for analysis.

For HPLC analysis, a Hewlett Packard 1100 HPLC, complete with a quaternary pump, vacuum degassing system, six-way injection valve, temperature regulated autosampler, column oven and Photodiode Array detector was used [Agilent Technologies available through Ultra Scientific Inc., 250 Smith Street, North Kingstown, R.I.]. The column was a Waters YMC 30, 5-micron, 4.6×250 mm with a guard column of the same material [Waters, 34 Maple Street, Milford, Mass.]. The solvents for the mobile phase were 81 methanol: 4 water: 15 tetrahydrofuran (THF) stabilized with 0.2% BHT (2,6-di-tert-butyl-4-methylphenol). Injections were 20 µl. Separation was isocratic at 30° C. with a flow rate of 1.7 ml/minute. The peak responses were measured by absorbance at 447 nm.

Using this protocol, the results from the first 2,546 samples were statistically analyzed to establish average values for lutein and zeaxanthin content. Because this was a semi-quantitative analytical screen, peak area values were used. To identify a mutant having a higher than average lutein and/or zeaxanthin concentration, a value of three standard deviations greater than the average was calculated. The calculated peak area means, standard deviations and zeaxanthin ratios are shown in Table 1, below.

TABLE 1

Lutein and Zeaxanthin Confidence Interval Calculations

| Statistic | Peak Area Lutein | Peak Area Zeaxanthin | Ratio (%) |
| --- | --- | --- | --- |
| Mean | 775.0 | 41.6 | 5.03 |
| Standard deviation (sd) | 263.2 | 16.4 | 0.71 |
| Mean + 3 sd | 1564.6 | 90.9 | 7.16 |

Based on the above values, samples were selected having lutein peak areas greater than 1565 and/or zeaxanthin peak areas greater than 91. Samples were also selected only for high lutein peak area, and for zeaxanthin ratios greater than 10 percent. A total of 88 mutants were identified from 21,754 assayed samples using these selection parameters. The total number of mutants resulting from each EMS seed treatment is shown in Table 2, below.

TABLE 2

Correlation of 'Scarletade' Mutants to EMS Treatment

| Selection Parameter | 0.4% EMS Treatment | 0.8% EMS Treatment | Total Plants |
| --- | --- | --- | --- |
| Zeaxanthin Ratio > 10% | 10 | 13 | 23 |
| Lutein >1566 and Zeaxanthin >91 | 18 | 10 | 28 |
| Lutein >1566 and Zeaxanthin <91 | 20 | 7 | 27 |
| Lutein <1566 and Zeaxanthin >91 | 7 | 3 | 10 |

More specific results of those assays as to relative levels of lutein and zeaxanthin are shown in Table 3, below.

TABLE 3

Identified 'Scarletade' Mutants

| Plant Identifier | Lutein Area | Zeaxanthin Area | Percent Zeaxanthin | Percent EMS Used |
| --- | --- | --- | --- | --- |
| 124-257 | 2.115 | 55.635 | 96.34 | 0.4 |
| 119-494 | 9.254 | 131.036 | 93.40 | 0.8 |
| 112-263 | 8.095 | 35.273 | 81.33 | 0.4 |
| 118-036 | 11.441 | 31.691 | 73.47 | 0.8 |
| 088-452 | 2.94 | 6.689 | 69.47 | 0.4 |
| 118-035 | 11.289 | 23.951 | 67.97 | 0.8 |
| 114-334 | 58.24 | 97.968 | 62.72 | 0.4 |
| 117-185 | 39.002 | 44.027 | 53.03 | 0.8 |
| 108-108 | 13.424 | 10.155 | 43.07 | 0.4 |
| 088-425 | 8.959 | 4.394 | 32.91 | 0.4 |
| 094-238 | 7.285 | 3.063 | 29.60 | 0.4 |
| 110-308 | 46.753 | 14.248 | 23.36 | 0.4 |
| 132-346 | 31.036 | 8.856 | 22.20 | 0.8 |
| 100-334 | 282.987 | 54.298 | 16.10 | 0.8 |
| 101-331 | 246.402 | 46.467 | 15.87 | 0.8 |
| 100-198 | 119.381 | 21.449 | 15.23 | 0.8 |
| 101-190 | 139.027 | 23.125 | 14.26 | 0.8 |
| 114-315 | 351.524 | 56.898 | 13.93 | 0.4 |
| 100-470 | 189.703 | 27.743 | 12.76 | 0.8 |
| 117-348 | 369.903 | 43.315 | 10.48 | 0.8 |
| 132-266 | 374.096 | 43.8 | 10.48 | 0.8 |
| 123-310 | 60.743 | 6.818 | 10.09 | 0.4 |
| 116-106 | 453.538 | 50.287 | 9.98 | 0.8 |

About 21,700 plants exhibited typical zeaxanthin ratios of about 4 to about 7 percent (about 1:25 to about 1:15). The above data illustrate the relative rarity of the mutations contemplated, as well as the almost equal number of plants that exhibit reduced zeaxanthin levels. The data also do not show a preference for the use of one level of mutagen versus the other used here.

EXAMPLE 3

EMS Treatment of *Tagetes erecta* 13819

Seeds of *Tagetes erecta* xanthophyll marigold named 13819 (a proprietary breeding selection of PanAmerican Seed Co. 622 Town Road, West Chicago, Ill. 60185) were treated with ethyl methanesulfonate (EMS, commercially available from Sigma Chemical Co. St. Louis, Mo. 63178).

Approximately, 7,000 seeds were added to 600 ml of 0.2% (v/v) or 0.4% (v/v) EMS and stirred gently for eight hours at ambient temperature. During a four-hour period following the EMS treatment, the seeds were washed sixteen times, each wash using continuous stirring with 600 ml distilled water.

The treated seeds, identified as $M_1$ seeds, were then sown in trays containing soilless potting mix. After three to four weeks, the seedlings were transplanted into the field. Flowers produced by these plants were bagged to prevent cross-pollination, and were permitted to spontaneously self-pollinate. The resulting seeds, identified as $M_2$ seeds, were harvested from approximately 2,391 plants. Of these plants, approximately 951 were grown from seeds treated with 0.2% EMS and approximately 1,440 were grown from seeds treated with 0.4% EMS.

To facilitate identification of mutant plants, the $M_2$ seeds from each of 50 plants were combined into one lot. This grouping resulted in a total of 48 seed lots. From late October through mid-November of the year 2000, 1000 seeds from each of 15 lots of the 0.4% EMS treatment were sown and 700 plants of each lot were greenhouse-grown at Seaview Nursery in El Rio, Calif. 93060. In addition, 1,500 seeds from all of the 48 lots were sown in late October of the year 2000, and 765 plants from each of the lots were field-grown at Semillas Pan American Chile LTDA, in Pichidegua, Chile.

EXAMPLE 4

HPLC Screening of EMS-Treated *Tagetes erecta* 13819

EMS-treated 13819 $M_2$ plants were greenhouse-grown at Seaview Nursery in El Rio, Calif. 93060 and field-grown at Semillas PanAmerican Chile LTDA, in Pichidegua, Chile, and were screened for altered zeaxanthin ratio. Flowers approximately 98% fully opened were selected for analysis. From these flowers, petals were removed one-third of the distance from the flower center. Approximately 100 mg of petal tissue was placed in plastic bags and stored frozen until analysis. Dry weight was determined for two petals that were placed in 3.5"×0.75" glass vials containing approximately 5 grams of glass beads.

For analysis, solvent delivery and aliquot removal were accomplished with a robotic system comprising a single injector valve Gilson 232XL and a 402 2S1V diluter. For saponification, 3 ml of 50% potassium hydroxide hydroethanolic solution (4 water: 1 ethanol) was added to each vial, followed by the addition of 3 ml octanol. The saponification treatment was conducted at room temperature with vials maintained on an IKA HS 501 horizontal shaker for fifteen hours at 250 movements per minute followed by a stationary phase of approximately one hour.

Following saponification, the supernatant was diluted with 0.9 ml of methanol. The addition of methanol was conducted under pressure to ensure sample homogeneity. Using a 0.25 ml syringe, a 0.1 ml aliquot was removed and transferred to HPLC vials for analysis.

For HPLC analysis, a Hewlett Packard 1100 complete with a quaternary pump, vacuum degassing system, six-way injection valve, temperature regulated autosampler, column oven and Photodiode Array detector was used. The column was a Waters YMC 30, 5-micron, 4.6×250 mm with a guard column of the same material. Standards were obtained from DHI-Water & Environment, DK-2970 Horsholm, Denmark and Sigma Chemical Co., St. Louis, Mo. 63178. The solvents for the mobile phase were 81 methanol: 4 water: 15 tetrahydrofuran stabilized with 0.2% BHT. Injections were 20 µl. Separation was isocratic at 30° C. with a flow rate of 1.7 ml/minute. The peak responses were measured at 447 nm.

Using this protocol, the results from the first 507 samples were statistically analyzed to establish average values for lutein and zeaxanthin content. To identify a mutant having a higher or lower than average lutein and zeaxanthin concentration, a value of three standard deviations greater than or less than the average was calculated. The calculated means, standard deviations and zeaxanthin ratios are shown in Table 4, below.

TABLE 4

| | Lutein and Zeaxanthin Confidence Interval Calculations | | | |
|---|---|---|---|---|
| Statistic | Lutein mg/g Fresh Weight | Zeaxanthin mg/g Fresh Weight | Lutein + Zeaxanthin mg/g Fresh Weight | Ratio (%) |
| Mean | 0.64 | 0.04 | 0.68 | 5.98 |
| Standard deviation | 0.14 | 0.01 | 0.147 | 1.1 |
| Mean + 3 sd | 1.06 | 0.07 | 1.12 | 9.28 |
| Mean − 3 sd | 0.22 | 0.007 | 0.24 | 2.68 |

Based on the above values, samples were selected having zeaxanthin ratios greater than 10 percent, combined lutein and zeaxanthin content greater than 1.12 mg/g fresh weight and combined lutein and zeaxanthin content less than 0.24 mg/g fresh weight. A total of 347 mutants were identified having a sum of lutein plus zeaxanthin greater than 1.12 mg/g, and 43 mutants having a zeaxanthin ratio greater than 10 percent were identified from 8192 samples using these selection parameters. The total number of mutants resulting from each EMS seed treatment is shown in Table 5, below.

TABLE 5

| Correlation of 13819 Mutants to EMS Treatment | | | |
|---|---|---|---|
| Selection Parameter | 0.2% EMS Treatment | 0.4% EMS Treatment | Total Plants |
| Zeaxanthin Ratio >10% | 2 | 41 | 43 |
| Lutein + Zeaxanthin > 1.12 mg/g dry weight | 6 | 341 | 347 |
| Lutein + Zeaxanthin < 0.24 mg/g dry weight | 2 | 175 | 177 |

Of the mutants having a zeaxanthin ratio greater than about 10 percent zeaxanthin, about 47 percent had between 10 and under 13 percent, whereas 53 percent exhibited 13 percent or greater.

EXAMPLE 5

Carotenoid Composition in Petals of Select Marigolds

Carotenoid compositions were determined for 'Scarletade' wild-type and mutant samples selected from those identified in the screening procedure described in Example 2. Petal samples were stored in a −80° C. freezer until mutants were identified. Samples were lyophilized, and the dried tissue was stored under argon at −80° C. until ready for analysis.

Extraction procedures were performed under red light. Dried petals were ground to pass through a No. 40 sieve mesh size. A ground sample was accurately weighed and transferred into a 100 ml red volumetric flask. To the sample, 500 microliters (μl) of $H_2O$ were added, and the mixture was swirled for 1 minute. Thirty ml of extractant solvent (10 ml hexane+7 ml acetone+6 ml absolute alcohol+7 ml toluene) were added, and the flask was shaken at 160 rpm for 10 minutes.

For saponification, 2 ml of 40% methanolic KOH were added into the flask, which was then swirled for one minute. The flask was placed in a 56° C. $H_2O$ bath for 20 minutes. An air condenser was attached to prevent loss of solvent. The sample was cooled in the dark for one hour with the condenser attached. After cooling, 30 ml of hexane were added, and the flask was shaken at 160 rpm for 10 minutes.

The shaken sample was diluted to volume (100 ml) with 10% sodium sulfate solution and shaken vigorously for one minute. The sample remained in the dark for at least 30 minutes. A 35 ml aliquot was removed from the approximately 50 ml upper phase, and transferred to a sample cup. An additional 30 ml of hexane were added into the flask that was then shaken at 160 rpm for 10 minutes. After approximately one hour, the upper phases were combined. For HPLC analysis, 10 ml aliquots were dried under nitrogen and stored under argon at −80° C.

HPLC equipment comprised an Alliance 2690 equipped with a refrigerated autosampler, column heater and a Waters Photodiode Array 996 detector (Waters Corp., 34 Maple Street Milford, Mass. 01757). Separation was obtained with a YMC $C_{30}$ column, 3 μm, 2.0×150 mm with a guard column of the same material. Standards were obtained from ICC Indofine Chemicals Somerville, N.J. 088876 and from DHI-Water & Environment, DK-2970 Horsholm, Denmark.

The dried mutant samples were resuspended in tetrahydrofuran and methanol to a total volume of 200 μl and filtered, whereas the control was not additionally concentrated. Carotenoids were separated using a gradient method. Initial gradient conditions were 90% methanol: 5% water: 5% methyl tert-butyl ether at a flow rate of 0.4 milliliters per minute (ml/min). From zero to 15 minutes, the mobile phase was changed from the initial conditions to 80 methanol: 5 water: 15 methyl tert-butyl ether, and from 15 to 60 minutes to 20 methanol: 5 water: 75 methyl tert-butyl ether. For the following 10 minutes, the mobile phase was returned to the initial conditions and the column equilibrated for an additional 10 minutes. The column temperature was maintained at 27° C. and the flow rate was 0.4 ml/minute. Injections were 10 μl. The majority of peak responses were measured at 450 nm and additional areas added from 286, 348, 400 and 472 nm extracted channels.

Values for carotenoid profiles of selected mutants are indicated in Tables 6a, 6b and 6c, below, using peak area as percent of the total area. Indicated compound identifications are based on spectra extracted and maximal absorbance in ethanol (lambda maxima; ETOH) obtained for major peaks in each chromatogram, some of which were verified by retention times of known standards. Values combine suspected isomers of the same compounds. Some compounds can contain minor impurities. Included in the Table are values for yellow colored American marigolds (yellow marigold) noted in Quackenbush et al., *J. Assoc. Off. Anal. Chem.*, 55(3):617–621 (1972). Single entries are used in Tables 6a–6c for neoxanthin/violaxanthin and chrysanthemaxanthin/flavoxanthin compound pairs that could not be separated by the procedure used here.

TABLE 6a

Relative Percent Distribution of Carotenoids
In Petals of *Tagetes erecta* and Mutants

| Carotenoid | Wavelength in EtOH (nm) | Marigold Selections | | | | | | | | | |
|---|---|---|---|---|---|---|---|---|---|---|---|
| | | Yellow Marigold | 'Scarletade' | 13819 | 117-185 | 124-257 | 119-494 | 112-263 | 118-035 | 088-425 | 325-444 |
| Phytoene | 276, 286, 297 | 2.4 | 0.3 | 0.3 | 6.8 | 7.0 | 1.0 | 11.0 | 12.3 | 34.3 | 30.9 |
| Phytofluene (isomers) | 331, 348, 367 | 2.6 | 0.5 | 0.4 | 4.0 | 4.2 | 0.9 | 7.5 | 7.4 | 17.8 | 13.3 |
| ζ-Carotene (cis/trans isomers) | 377, 399, 425 | nf* | <0.1 | <0.1 | 5.6 | 5.3 | 1.3 | 6.9 | 6.8 | 18.2 | 17.1 |
| Neurosporene | 416, 440, 470 | nr** | <0.1 | <0.1 | 0.1 | 0.2 | <0.1 | <0.1 | <0.1 | 3.5 | 3.5 |
| Lycopene | 447, 472, 504 | nr | <0.1 | <0.1 | 0.5 | 1.3 | <0.1 | <0.1 | <0.1 | 1.0 | 2.8 |
| α-Carotene | 423, 444, 473 | 0.1 | <0.1 | <0.1 | <0.1 | <0.1 | <0.1 | <0.1 | <0.1 | 0.8 | 1.2 |
| β-Carotene | 425, 451, 478 | 0.5 | <0.1 | <0.1 | 4.4 | 6.8 | 2.3 | 0.6 | 0.3 | 2.3 | 4.8 |
| Neoxanthin | 415, 439, 467 | 0.8 | 1.5 | 4.1 | 13.3 | 12.8 | 16.7 | 4.3 | 3.5 | 0.7 | 1.1 |
| Violaxanthin | 419, 440, 470 | nr | | | | | | | | | |
| Antheraxanthin | 422, 444, 472 | 0.1 | 3.1 | 5.5 | 12.5 | 14.4 | 19.2 | 4.1 | 4.5 | 0.9 | 1.5 |
| Lutein | 420, 445, 475 | 72.3 | 84.9 | 81.7 | 13.3 | 1.3 | <0.1 | 0.6 | 7.1 | 2.0 | 4.9 |
| Zeaxanthin | 428, 450, 478 | 16.4 | 4.7 | 5.9 | 21.3 | 30.6 | 35.7 | 16.5 | 18.2 | 2.0 | 4.0 |

TABLE 6a-continued

Relative Percent Distribution of Carotenoids
In Petals of *Tagetes erecta* and Mutants

| Carotenoid | Wavelength in EtOH (nm) | Marigold Selections ||||||||||
|---|---|---|---|---|---|---|---|---|---|---|---|
| | | Yellow Marigold | 'Scarletade' | 13819 | 117-185 | 124-257 | 119-494 | 112-263 | 118-035 | 088-425 | 325-444 |
| α-Cryptoxanthin | 421, 446, 475 | 0.8 | <0.1 | <0.1 | <0.1 | <0.1 | <0.1 | 32.2 | 26.9 | <0.1 | 0.2 |
| β-Cryptoxanthin | 428, 450, 478 | 0.5 | <0.1 | <0.1 | 0.5 | 0.6 | 0.8 | 0.2 | 0.4 | 1.9 | 1.8 |
| β-Zeacarotene | 406, 428, 454 | 0.5 | | | | not identified | | | | | |
| Chrysanthemaxanthin | 400, 421, 448 | 0.8 | <0.1 | <0.1 | 2.3 | 1.5 | 4.5 | 0.8 | 0.5 | 0.2 | 0.2 |
| Flavoxanthin | 400, 421, 448 | 1.3 | | | | | | | | | |
| Auroxanthin | 380, 401, 426 | 0.1 | | | | not identified | | | | | |
| Other compounds that show absorbance at 450 nm | | 0.8 | 5.0 | 2.1 | 15.3 | 14.0 | 17.6 | 15.1 | 12.0 | 14.3 | 12.7 |

*nf = not found
**nr = not reported

TABLE 6b

Relative Percent Distribution of Carotenoids In
Petals of *Tagetes erecta* and Mutants

| Carotenoid | Wavelength in EtOH (nm) | Marigold Selections |||||||
|---|---|---|---|---|---|---|---|---|
| | | Yellow Marigold | 'Scarletade' | 13819 | 100-198 | 100-334 | 100-470 | 101-190 | 114-315 |
| Phytoene (isomers) | 276, 286, 297 | 2.4 | 0.3 | 0.3 | 4.8 | 3.9 | 6.1 | 3.4 | 5.2 |
| Phytofluene (isomers) | 331, 348, 367 | 2.6 | 0.5 | 0.4 | 3.2 | 3.2 | 3.8 | 3.2 | 3.3 |
| ζ-Carotene (cis/trans isomers) | 377, 399, 425 | nf* | <0.1 | <0.1 | 4.8 | 4.0 | 4.4 | 3.6 | 3.2 |
| Neurosporene | 416, 440, 470 | nr** | <0.1 | <0.1 | <0.1 | <0.1 | <0.1 | <0.1 | <0.1 |
| Lycopene | 447, 472, 504 | nr | <0.1 | <0.1 | <0.1 | <0.1 | <0.1 | <0.1 | <0.1 |
| α-Carotene | 423, 444, 473 | 0.1 | <0.1 | <0.1 | 0.3 | 0.4 | 0.2 | 0.4 | 0.2 |
| β-Carotene | 425, 451, 478 | 0.5 | <0.1 | <0.1 | 0.8 | 0.7 | 0.5 | 0.8 | 0.5 |
| Neoxanthin | 415, 439, 467 | 0.8 | 1.5 | 4.1 | <0.2 | 0.3 | <0.2 | <0.2 | <0.2 |
| Violaxanthin | 419, 440, 470 | nr | | | | | | | |
| Antheraxanthin | 422, 444, 472 | 0.1 | 3.1 | 5.5 | <0.2 | <0.2 | <0.2 | <0.2 | <0.2 |
| Lutein | 420, 445, 475 | 72.3 | 84.9 | 81.7 | 68.0 | 70.7 | 67.5 | 71.1 | 71.6 |
| Zeaxanthin | 428, 450, 478 | 16.4 | 4.7 | 5.9 | 14.8 | 13.4 | 13.1 | 13.6 | 12.3 |
| α-Cryptoxanthin | 421, 446, 475 | 0.8 | <0.1 | <0.1 | 0.6 | 0.6 | 0.5 | 0.6 | 0.4 |
| δ-Carotene | 431, 456, 489 | nr | <0.1 | <0.1 | 0.5 | 0.2 | 0.8 | 0.4 | 0.5 |
| β-Cryptoxanthin | 428, 450, 478 | 0.5 | <0.1 | <0.1 | <0.2 | <0.2 | <0.2 | <0.2 | <0.2 |
| β-Zeacarotene | 406, 428, 454 | 0.5 | | | not identified | | | | |
| Chrysanthemaxanthin | 400, 421, 448 | 0.8 | <0.1 | <0.1 | <0.2 | <0.2 | <0.2 | <0.2 | <0.2 |
| Flavoxanthin | 400, 421, 448 | 1.3 | | | | | | | |

TABLE 6b-continued

Relative Percent Distribution of Carotenoids In Petals of *Tagetes erecta* and Mutants

| Carotenoid | Wavelength in EtOH (nm) | Marigold Selections | | | | | | | |
|---|---|---|---|---|---|---|---|---|---|
| | | Yellow Marigold | 'Scarletade' | 13819 | 100-198 | 100-334 | 100-470 | 101-190 | 114-315 |
| Auroxanthin | 380, 401, 426 | 0.1 | | | not identified | | | | |
| Other compounds that show absorbance at 450 nm | | 0.8 | 5.0 | 2.1 | 2.1 | 2.6 | 2.9 | 2.8 | 2.7 |

*nf = not found
**nr = not reported

TABLE 6c

Relative Percent Distribution of Carotenoids In Petals of *Tagetes erecta* and Mutants

| Carotenoid | Wavelength in EtOH (nm) | Marigold Selections | | | | | | |
|---|---|---|---|---|---|---|---|---|
| | | Yellow Marigold | 'Scarletade' | 13819 | 126-415 | 098-240 | 098-394 | 115-004 |
| Phytoene (isomers) | 276, 286, 297 | 2.4 | 0.3 | 0.3 | 11.8 | 10.0 | 8.6 | 13.0 |
| Phytofluene (isomers) | 331, 348, 367 | 2.6 | 0.5 | 0.4 | 9.1 | 5.8 | 5.4 | 9.6 |
| ζ-Carotene (cis/trans isomers) | 377, 399, 425 | nf* | <0.1 | <0.1 | 5.0 | 3.6 | 3.5 | 10.3 |
| Neurosporene | 416, 440, 470 | nr** | <0.1 | <0.1 | <0.1 | <0.1 | <0.1 | <0.1 |
| Lycopene | 447, 472, 504 | nr | <0.1 | <0.1 | <0.1 | <0.1 | <0.1 | <0.1 |
| α-Carotene | 423, 444, 473 | nr | <0.1 | <0.1 | 0.5 | 0.4 | 0.4 | 0.6 |
| β-Carotene | 425, 451, 478 | 0.5 | <0.1 | <0.1 | 0.1 | 0.1 | 0.1 | <0.1 |
| Neoxanthin | 415, 439, 467 | 0.8 | 1.5 | 4.1 | 0.3 | 0.4 | 0.4 | <0.1 |
| Violaxanthin | 419, 440, 470 | nr | | | | | | |
| Antheraxanthin | 422, 444, 472 | 0.1 | 3.1 | 5.5 | 1.7 | 1.9 | 2.2 | 1.9 |
| Lutein | 420, 445, 475 | 72.3 | 84.9 | 81.7 | 61.7 | 70.1 | 71.0 | 52.3 |
| Zeaxanthin | 428, 450, 478 | 16.4 | 4.7 | 5.9 | 2.5 | 2.8 | 3.4 | 1.8 |
| α-Cryptoxanthin | 421, 446, 475 | 0.8 | <0.1 | <0.1 | 0.7 | 0.6 | 0.4 | 0.2 |
| δ-Carotene | 431, 456, 489 | nr | <0.1 | <0.1 | 1.6 | 0.4 | 0.3 | 5.2 |
| β-Cryptoxanthin | 428, 450, 478 | 0.1 | <0.1 | <0.1 | <0.1 | <0.1 | <0.1 | <0.1 |
| β-Zeacarotene | 406, 428, 454 | 0.5 | | | not identified | | | |
| Chrysanthemaxanthin | 400, 421, 448 | 0.8 | <0.1 | <0.1 | <0.1 | 0.1 | 0.1 | <0.1 |
| Flavoxanthin | 400, 421, 448 | 1.4 | | | | | | |
| Auroxanthin | 380, 401, 426 | 0.1 | | | not identified | | | |
| Other compounds that show absorbance at 450 nm | | 0.8 | 5.0 | 2.1 | 4.9 | 3.7 | 4.19 | 4.8 |

*nf = not found
**nr = not reported

EXAMPLE 6

Preparation of Marigolds with Little Lutein and High Zeaxanthin, Phytoene, Lycopene or β-Carotene Levels Through Breeding of Mutants Marigold mutant selection 124–257 that exhibits an increased zeaxanthin to lutein ratio compared to wild type was selfed and the resulting seed was maintained. Plants from the selfing of marigold selection 124–257 were used as male parents in a cross with female parent PanAmerican Seed proprietary breeding line F9 Ap(85368–4). From this cross, $F_1$ plants were produced and selfed to yield an $F_2$ population.

Fifteen seedlings from the $F_2$ cross were analyzed for the absence of lutein using thin layer chromatography (TLC). Approximately 50 mg of fresh leaf tissue from each seedling was weighed into a 100×13 mm screw top tube containing five glass beads. Sealed vials were stored at −20° C.

For analysis, 500 μl of extractant solvent (10 ml hexane+7 ml acetone+6 ml absolute alcohol+7 ml toluene) were added, and the sealed tubes were vortexed for a minimum of 45 minutes. After vortexing, the solution was transferred to a 4 ml amber vial and evaporated under nitrogen. Samples were resuspended in 125 μl of the above-described extraction solvent and 10 μl were spotted on 19 channel silica gel plates. Plates were dried for approximately 10 minutes then developed for 25 minutes in a two channel 25 cm developing tank containing 100 ml of a 2:1 ethyl acetate:hexane solution. Upon removal, samples were evaluated for the absence of lutein.

From this screen, $F_2$ marigold selection 14649–3 was identified. This selection was used as the female parent in crosses with mutants 101–190 and 100–198, which exhibit an increased zeaxanthin to lutein ratio in addition to having reduced epoxycarotenoid (e.g., neoxanthin and violaxanthin) production compared to wild type.

Marigold mutant selection 100–198 was selfed and the resulting seed was maintained. Plants from the selfing of marigold selection 100–198 were used as the male parent in a cross with the female parent selection 14649-3 described above. From this cross, $F_1$ seeds were collected, and of these 30 seeds were planted. Eleven of the resulting plants were selfed. From this cross, $F_2$ seeds were collected, and 400 of those seeds were planted and grown.

TLC analysis, as described above, was used to analyze leaves of 151 seedlings. Thirty-two plants were identified based on reduced epoxycarotenoid production typical of mutant selection 100–198. The remaining TLC extract was analyzed using high performance liquid chromatography (HPLC), performed using a modified Example 5 protocol. Modifications include the following: dried samples were resuspended into methyl tert-butyl ether and methanol, all gradient conditions used water increased to 6 percent with a corresponding 1 percent decrease in methanol, and column temperature was maintained at 25° C.

Analysis confirmed that seven of the 32 plants exhibited an increased zeaxanthin to lutein ratio typical of mutant selection 124–257. Petal and leaf samples of the seven selections were extracted and analyzed according to the protocol in Example 5 with modifications noted above. The results for petals are shown in Table 7a, below. In addition, non-saponified petal samples were analyzed to determine the percentage, if any, of non-esterified zeaxanthin. Those data are presented in Table 9.

Marigold mutant selection 101–190 was selfed and the resulting seed was maintained. Marigold selection 101–190 was used as the male parent in a cross with the female parent selection 14649–3 described above. From this cross, $F_1$ seeds were collected and of those seeds, 30 were planted. Six of the resulting plants were selfed. From this latter cross, $F_2$ seeds were collected, planted and grown.

It was determined that the current TLC analysis method was inconclusive for this population. Therefore, approximately 30 plants were selected for HPLC analysis based on having an orange-colored sepal phenotype.

Samples were extracted as for TLC; however, HPLC analysis was conducted. Ten of the 30 selections were found to have reduced epoxy-carotenoid production typical of mutant selection 101–190 in addition to having an increased zeaxanthin to lutein ratio typical of selection 124–257.

Petal and leaf samples of the ten selections were extracted and analyzed according to the protocol in Example 5 with modifications noted above. The results for petals are shown in Tables 7b and 7c. In addition, non-saponified petal samples were analyzed to determine the percentage of non-esterified zeaxanthin. Those data are presented in Table 8.

TABLE 7a

Relative Percent Distribution of Carotenoids
In Petals of *Tagetes erecta* and Mutant Crosses

| Carotenoid | Wavelength in EtOH (nm) | 'Scarletade' | 124-257 | 100-198 | 27772-029 | 27772-036 | 27772-100 | 27772-109 | 27772-123 | 27772-130 | 27772-134 |
|---|---|---|---|---|---|---|---|---|---|---|---|
| Phytoene (isomers) | 276, 286, 297 | 0.5 | 3.9 | 4.5 | 4.9 | 9.2 | 7.0 | 5.1 | 5.6 | 5.7 | 11.7 |
| Phytofluene (isomers) | 331, 348, 367 | 0.7 | 3.6 | 4.4 | 4.6 | 7.2 | 5.7 | 4.6 | 5.3 | 5.0 | 8.2 |
| ζ-Carotene (cis/trans isomers) | 377, 399, 425 | <0.2 | 3.3 | 4.1 | 4.8 | 10.6 | 5.2 | 4.5 | 5.0 | 4.4 | 7.4 |
| Neurosporene | 416, 440, 470 | <0.2 | <0.2 | <0.2 | 0.2 | 0.4 | 0.3 | <0.2 | 0.2 | 0.3 | 0.4 |
| Lycopene | 447, 472, 504 | <0.2 | 0.5 | <0.2 | 0.3 | 1.4 | 0.9 | <0.2 | 0.6 | 0.3 | 0.9 |
| α-Carotene | 423, 444, 473 | <0.2 | <0.2 | 0.4 | <0.2 | <0.2 | <0.2 | <0.2 | <0.2 | <0.2 | <0.2 |

TABLE 7a-continued

Relative Percent Distribution of Carotenoids
In Petals of *Tagetes erecta* and Mutant Crosses

| Carotenoid | Wavelength in EtOH (nm) | Marigold Selections |||||||||
|---|---|---|---|---|---|---|---|---|---|---|
| | | 'Scarletade' | 124-257 | 100-198 | 27772-029 | 27772-036 | 27772-100 | 27772-109 | 27772-123 | 27772-130 | 27772-134 |
| β-Carotene | 425, 451, 478 | <0.2 | 7.4 | 1.3 | 6.3 | 6.1 | 4.9 | 4.5 | 4.2 | 5.0 | 4.8 |
| Neoxanthin | 415, 439, 467 | 0.5 | 3.4 | <0.2 | <0.2 | <0.2 | <0.2 | <0.2 | <0.2 | <0.2 | <0.2 |
| Violaxanthin | 419, 440, 470 | 0.7 | 12.7 | <0.2 | <0.2 | <0.2 | <0.2 | <0.2 | <0.2 | 0.2 | <0.2 |
| Antheraxanthin | 422, 444, 472 | 1.6 | 17.5 | 0.6 | 0.5 | 0.4 | 0.6 | 0.5 | 0.5 | 0.7 | 0.3 |
| Lutein | 420, 445, 475 | 91.0 | 2.3 | 68.1 | 0.5 | 0.5 | 0.5 | 0.4 | 0.4 | 0.6 | 0.4 |
| Zeaxanthin | 428, 450, 478 | 3.3 | 29.8 | 14.3 | 73.8 | 60.0 | 70.3 | 76.5 | 74.3 | 72.4 | 62.0 |
| α-Cryptoxanthin | 421, 446, 475 | <0.2 | <0.2 | <0.2 | <0.2 | <0.2 | <0.2 | <0.2 | <0.2 | <0.2 | <0.2 |
| δ-Carotene | 431, 456, 489 | <0.2 | <0.2 | 0.7 | <0.2 | <0.2 | <0.2 | <0.2 | <0.2 | 0.3 | <0.2 |
| β-Cryptoxanthin | 428, 450, 478 | <0.2 | 1.0 | <0.2 | 1.1 | 1.0 | 1.1 | 1.4 | 1.1 | 1.1 | 1.1 |
| β-Zeacarotene | 406, 428, 454 | | | | Not identified ||||| | |
| Chrysanthemaxanthin | 400, 421, 448 | <0.2 | 1.7 | <0.2 | <0.2 | <0.2 | <0.2 | <0.2 | <0.2 | <0.2 | <0.2 |
| Flavoxanthin | 400, 421, 448 | | | | | | | | | | |
| Auroxanthin | 380, 401, 426 | | | | Not identified ||||| | |
| Other compounds that show absorbance at 450 nm | | 1.7 | 12.9 | 1.6 | 2.8 | 3.2 | 3.5 | 2.4 | 2.7 | 4.2 | 2.8 |

TABLE 7b

Relative Percent Distribution of Carotenoids
In Petals of *Tagetes erecta* and Mutant Crosses

| Carotenoid | Wavelength in EtOH (nm) | Marigold Selections ||||||||
|---|---|---|---|---|---|---|---|---|---|
| | | 'Scarletade' | 124-257 | 101-190 | 27773-006 | 27773-030 | 27773-087 | 27773-107 | 27773-128 |
| Phytoene (isomers) | 276, 286, 297 | 0.5 | 3.9 | 3.9 | 3.2 | 5.9 | 6.8 | 8.3 | 4.9 |
| Phytofluene (isomers) | 331, 348, 367 | 0.7 | 3.6 | 4.6 | 3.8 | 5.8 | 7.2 | 7.3 | 4.9 |
| ζ-Carotene (cis/trans isomers) | 377, 399, 425 | <0.2 | 3.3 | 5.1 | 4.4 | 5.0 | 10.4 | 8.6 | 5.0 |
| Neurosporene | 416, 440, 470 | <0.2 | <0.2 | <0.2 | <0.2 | 0.2 | <0.2 | <0.2 | <0.2 |
| Lycopene | 447, 472, 504 | <0.2 | 0.5 | <0.2 | 0.2 | 0.4 | 0.8 | <0.2 | 0.4 |
| α-Carotene | 423, 444, 473 | <0.2 | <0.2 | 0.3 | <0.2 | <0.2 | <0.2 | <0.2 | <0.2 |
| β-Carotene | 425, 451, 478 | <0.2 | 7.4 | 1.6 | 9.8 | 8.9 | 11.7 | 8.0 | 7.1 |
| Neoxanthin | 415, 439, 467 | 0.5 | 3.4 | <0.2 | <0.2 | <0.2 | <0.2 | <0.2 | <0.2 |
| Violaxanthin | 419, 440, 470 | 0.7 | 12.7 | <0.2 | <0.2 | <0.2 | <0.2 | <0.2 | <0.2 |
| Antheraxanthin | 422, 444, 472 | 1.6 | 17.5 | 0.6 | 1.9 | 1.8 | 0.9 | 0.8 | 2.1 |
| Lutein | 420, 445, 475 | 91.0 | 2.3 | 63.8 | 0.8 | 0.6 | 0.9 | 0.7 | 0.6 |
| Zeaxanthin | 428, 450, 478 | 3.3 | 29.8 | 16.8 | 69.4 | 67.9 | 58.5 | 62.4 | 70.3 |

TABLE 7b-continued

Relative Percent Distribution of Carotenoids
In Petals of *Tagetes erecta* and Mutant Crosses

| Carotenoid | Wavelength in EtOH (nm) | Marigold Selections | | | | | | | |
|---|---|---|---|---|---|---|---|---|---|
| | | 'Scarletade' | 124-257 | 101-190 | 27773-006 | 27773-030 | 27773-087 | 27773-107 | 27773-128 |
| α-Cryptoxanthin | 421, 446, 475 | <0.2 | <0.2 | <0.2 | <0.2 | <0.2 | <0.2 | <0.2 | <0.2 |
| δ-Carotene | 431, 456, 489 | <0.2 | <0.2 | 0.2 | 0.9 | <0.2 | 0.2 | 0.4 | <0.2 |
| β-Cryptoxanthin | 428, 450, 478 | <0.2 | 1.0 | 0.2 | 1.1 | 1.2 | 1.1 | 1.5 | 1.3 |
| β-Zeacarotene | 406, 428, 454 | | | | not identified | | | | |
| Chrysanthemaxanthin | 400, 421, 448 | <0.2 | 1.7 | <0.2 | <0.2 | <0.2 | <0.2 | <0.2 | <0.2 |
| Flavoxanthin | 400, 421, 448 | | | | | | | | |
| Auroxanthin | 380, 401, 426 | | | | not identified | | | | |
| Other compounds that show absorbance at 450 nm | | 1.7 | 12.9 | 2.8 | 4.1 | 2.2 | 1.5 | 1.7 | 3.2 |

TABLE 7c

Relative Percent Distribution of Carotenoids
in Petals of *Tagetes erecta* and Mutant Crosses

| Carotenoid | Wavelength in EtOH (nm) | Marigold Selections | | | | | | | |
|---|---|---|---|---|---|---|---|---|---|
| | | 'Scarletade' | 124-257 | 101-190 | 27774-008 | 27774-050 | 27774-064 | 27774-076 | 27774-123 |
| Phytoene (isomers) | 276, 286, 297 | 0.5 | 3.9 | 3.9 | 4.4 | 5.2 | 7.0 | 8.8 | 5.6 |
| Phytofluene (isomers) | 331, 348, 367 | 0.7 | 3.6 | 4.6 | 4.6 | 5.7 | 6.0 | 8.8 | 5.5 |
| ζ-Carotene (cis/trans isomers) | 377, 399, 425 | <0.2 | 3.3 | 5.1 | 4.2 | 8.5 | 6.0 | 9.8 | 5.9 |
| Neurosporene | 416, 440, 470 | <0.2 | <0.2 | <0.2 | 0.2 | <0.2 | 0.3 | 0.3 | <0.2 |
| Lycopene | 447, 472, 504 | <0.2 | 0.5 | <0.2 | 0.4 | 0.6 | 0.4 | 1.5 | 0.2 |
| α-Carotene | 423, 444, 473 | <0.2 | <0.2 | 0.3 | <0.2 | <0.2 | <0.2 | <0.2 | <0.2 |
| β-Carotene | 425, 451, 478 | <0.2 | 7.4 | 1.6 | 7.0 | 9.5 | 5.8 | 9.9 | 10.1 |
| Neoxanthin | 415, 439, 467 | 0.5 | 3.4 | <0.2 | <0.2 | <0.2 | <0.2 | <0.2 | <0.2 |
| Violaxanthin | 419, 440, 470 | 0.7 | 12.7 | <0.2 | <0.2 | <0.2 | <0.2 | <0.2 | <0.2 |
| Antheraxanthin | 422, 444, 472 | 1.6 | 17.5 | 0.6 | 2.5 | <0.2 | 1.5 | 1.9 | 2.5 |
| Lutein | 420, 445, 475 | 91.0 | 2.3 | 63.8 | 0.8 | 0.8 | 0.7 | 0.6 | 0.8 |
| Zeaxanthin | 428, 450, 478 | 3.3 | 29.8 | 16.8 | 71.2 | 66.9 | 67.8 | 54.3 | 64.3 |
| α-Cryptoxanthin | 421, 446, 475 | <0.2 | <0.2 | <0.2 | <0.2 | <0.2 | <0.2 | <0.2 | <0.2 |
| δ-Carotene | 431, 456, 489 | <0.2 | <0.2 | 0.2 | <0.2 | <0.2 | <0.2 | <0.2 | <0.2 |
| β-Cryptoxanthin | 428, 450, 478 | <0.2 | 1.0 | 0.2 | 1.1 | 1.0 | 1.6 | 1.3 | 1.3 |
| β-Zeacarotene | 406, 428, 454 | | | | not identified | | | | |
| Chrysanthemaxanthin | 400, 421, 448 | <0.2 | 1.7 | <0.2 | <0.2 | <0.2 | <0.2 | <0.2 | <0.2 |
| Flavoxanthin | 400, 421, 448 | | | | | | | | |

TABLE 7c-continued

Relative Percent Distribution of Carotenoids
in Petals of *Tagetes erecta* and Mutant Crosses

| Carotenoid | Wavelength in EtOH (nm) | Marigold Selections | | | | | | |
|---|---|---|---|---|---|---|---|---|
| | | 'Scarletade' | 124-257 | 101-190 | 27774-008 | 27774-050 | 27774-064 | 27774-076 | 27774-123 |
| Auroxanthin | 380, 401, 426 | not identified | | | | | | | |
| Other compounds that show absorbance at 450 nm | | 1.7 | 12.9 | 2.8 | 3.6 | 1.3 | 2.9 | 2.4 | 3.4 |

TABLE 8

Relative Percent Non-esterified Zeaxanthin In
Petals of *Tagetes erecta* And Mutant Crosses

| Marigold Selection | % Non-esterified Zeaxanthin |
|---|---|
| 'Scarletade' | 0 |
| 124-257 | 1.1 |
| 100-198 | 2.2 |
| 101-190 | 1.6 |
| 27772-029 | 6.8 |
| 27772-036 | 5.8 |
| 27772-100 | 7.9 |
| 27772-109 | 13.0 |
| 27772-123 | 7.3 |
| 27772-130 | 6.4 |
| 27772-134 | 5.0 |
| 27773-006 | 8.1 |
| 27773-030 | 3.2 |
| 27773-087 | 13.6 |
| 27773-107 | 19.3 |
| 27773-128 | 7.4 |
| 27774-008 | 3.9 |
| 27774-050 | 9.1 |
| 27774-064 | 6.3 |
| 27774-076 | 4.5 |
| 27774-123 | 6.8 |

EXAMPLE 7

Purification of Mixed Zeaxanthin Esters

One kilo of dried marigold corollas, having a mixed zeaxanthin ester content of 1.0 wt percent as is determined on an aliquot by Soxhlet extraction and subsequent spectrophotometric measurement at 445 nm, which is the wavelength of maximum optical absorption, is percolated with 8 liters of hexane using a glass column fitted with a ceramic filter. The hexane of the resulting extractant solution is evaporated at 60° C. under vacuum. Thirty-five grams of oleoresin having a mixed zeaxanthin ester content of 9.0 percent, as determined by HPLC peak areas, are obtained.

The oleoresin is stirred for 3 hours with 100 ml of isopropanol at 20° C. The resulting suspension is filtered through filter paper, and the solvent is removed under vacuum at ambient temperature. The resulting solid is melted at 65° C. and poured into a mold. After 3 hours of cooling to ambient temperature, one mixed zeaxanthin ester bar weighing 5 grams and having a mixed zeaxanthin ester content of approximately 16 wt. percent (by spectrophotometry in hexane) is obtained. Alternatively, the mixed zeaxanthin concentrate is ground into a granular state.

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed is:

1. A purified carotenoid concentrate comprising a mixture of zeaxanthin $C_8$–$C_{20}$ carboxylic acid esters extracted from *Tagetes erecta* in which the mixture of zeaxanthin esters constitute about 50 mg/g or more of the concentrate and wherein the zeaxanthin portion of the ester is about 20 percent or more of the total carotenoids present when assayed after saponification, said concentrate being in the form of a solid or gum.

2. The carotenoid concentrate according to claim 1 wherein said zeaxanthin esters are monoesterified zeaxanthin, diesterified zeaxanthin or mixtures thereof.

3. The carotenoid concentrate according to claim 1 wherein the acid portion of the mixture of zeaxanthin esters comprises a plurality of acids selected from the group consisting of palmitic, stearic, myristic, oleic, linoleic, linolenic, lauric, palmitoleic, pentadecanoic, and capric acids.

4. The carotenoid concentrate according to claim 1 wherein said zeaxanthin is about 25 percent or more of the total carotenoids present when assayed after saponification.

5. The carotenoid concentrate according to claim 1 wherein said total carotenoids include at least one additional carotenoid in free or esterified form.

6. The carotenoid concentrate according to claim 5 wherein said additional carotenoid is selected from the group consisting of a carotene, a xanthophyll, a monoesterified xanthophyll, a diesterified xanthophyll and mixtures thereof.

7. A diluted purified carotenoid composition comprising a mixture of zeaxanthin $C_8$–$C_{20}$ carboxylic acid esters extracted from *Tagetes erecta* dissolved or dispersed in a comestible diluent in which the mixture of zeaxanthin esters constitute about 10 mg/g or more of the diluted composition and wherein the zeaxanthin portion of the ester is about 20 percent or more of the total carotenoids present when assayed after saponification.

8. The carotenoid composition according to claim 7 wherein said comestible diluent is an oil.

9. The carotenoid composition according to claim 7 wherein said composition is present encapsulated within a beadlet.

10. The carotenoid composition according to claim 7 wherein said zeaxanthin esters are monoesterified zeaxanthin, diesterified zeaxanthin or mixtures thereof.

11. The carotenoid composition according to claim 7 wherein the acid portion of the mixture of zeaxanthin esters comprises a plurality of acids selected from the group consisting of palmitic, stearic, myristic, oleic, linoleic, linolenic, lauric, palmitoleic, pentadecanoic, and capric acids.

12. The carotenoid composition according to claim 7 wherein said zeaxanthin portion of the ester is about 25 percent or more of the total carotenoids present when assayed after saponification.

13. The carotenoid composition according to claim 7 wherein said total carotenoids include at least one additional carotenoid in free or esterified form.

14. The carotenoid composition according to claim 13 wherein said additional carotenoid is selected from the group consisting of a carotene, a xanthophyll, a monoesterified xanthophyll, a diesterified xanthophyll and mixtures thereof.

15. A diluted purified carotenoid composition comprising a mixture of zeaxanthin $C_8$–$C_{20}$ carboxylic acid esters extracted from *Tagetes erecta* dissolved or dispersed in a cosmetically acceptable diluent in which the mixture of zeaxanthin esters constitute about 10 mg/g or more of the diluted composition and wherein the zeaxanthin portion of the ester is about 20 percent or more of the total carotenoids present when assayed after saponification.

16. The carotenoid composition according to claim 15 wherein said zeaxanthin esters are monoesterified zeaxanthin, diesterified zeaxanthin or mixtures thereof.

17. The carotenoid composition according to claim 15 wherein the acid portion of the mixture of zeaxanthin esters comprises a plurality of acids selected from the group consisting of palmitic, stearic, myristic, oleic, linoleic, linolenic, lauric, palmitoleic, pentadecanoic, and capric acids.

18. The carotenoid composition according to claim 15 wherein said zeaxanthin portion of the ester is about 25 percent or more of the total carotenoids present when assayed after saponification.

19. The carotenoid composition according to claim 15 wherein said total carotenoids include at least one additional carotenoid in free or esterified form.

20. The carotenoid composition according to claim 19 wherein said additional carotenoid is selected from the group consisting of a carotene, a xanthophyll, a monoesterified xanthophyll, a diesterified xanthophyll and mixtures thereof.

21. A topical cream, lotion, or ointment that contains a diluted purified *Tagetes erecta* extract that comprises a mixture of zeaxanthin $C_8$–$C_{20}$ carboxylic acid esters dissolved or dispersed in a diluent and present in a light protection effective amount.

* * * * *